United States Patent
Gelo-Pujic et al.

(10) Patent No.: US 10,280,407 B2
(45) Date of Patent: May 7, 2019

(54) MICROORGANISMS AND METHODS FOR PRODUCING VANILLIN

(71) Applicant: RHODIA OPERATIONS, Paris (FR)

(72) Inventors: Mirjana Gelo-Pujic, Serezin-sur-Rhone (FR); Antoine Amory, Limal (BE)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/322,745

(22) PCT Filed: Jun. 30, 2015

(86) PCT No.: PCT/EP2015/064801
§ 371 (c)(1),
(2) Date: Dec. 29, 2016

(87) PCT Pub. No.: WO2016/001203
PCT Pub. Date: Jan. 7, 2016

(65) Prior Publication Data
US 2017/0137787 A1 May 18, 2017

(30) Foreign Application Priority Data
Jul. 1, 2014 (EP) .................................... 14306069

(51) Int. Cl.
*C12N 9/04* (2006.01)
*C12P 7/24* (2006.01)
*C12R 1/01* (2006.01)
*C12N 15/76* (2006.01)

(52) U.S. Cl.
CPC .......... *C12N 9/0006* (2013.01); *C12N 15/76* (2013.01); *C12P 7/24* (2013.01); *C12R 1/01* (2013.01)

(58) Field of Classification Search
None
See application file for complete search history.

(56) References Cited

U.S. PATENT DOCUMENTS

2014/0087428 A1* 3/2014 Lambrecht ........... C12N 9/0008
435/92

FOREIGN PATENT DOCUMENTS

| JP | 2004 267131 A | 9/2004 |
| WO | 03/071861 A2 | 9/2003 |
| WO | 2012/172108 A1 | 12/2012 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Chica et al., Semi-rational approaches to engineering enzyme activity: combining the benefits of directed evolution and rational design. Curr. Opi. Biotechnol., 2005, vol. 16: 378-384.*
Kisselev L., Polypeptide release factors in prokaryotes and eukaryotes: same function, different structure. Structure, 2002, vol. 10: 8-9.*
Klenk et al. "Genome sequence of the soil bacterium *Saccharomonospora azurea* type strain (NA-128(T))."; Stand. Genomic Sci. 6:220-229(2012).*

* cited by examiner

Primary Examiner — Iqbal H Chowdhury
(74) Attorney, Agent, or Firm — W & C IP

(57) ABSTRACT

The present invention concerns a recombinant strain belonging to the order of Actinomycetales, wherein at least one gene encoding an enzyme having vanillin reductase activity is non-functional. The present invention is also related to a process for producing vanillin or a precursor thereof, comprising the culture of a recombinant strain in an appropriate medium comprising a substrate, and recovery of the produced vanillin or precursor thereof.

22 Claims, 4 Drawing Sheets

Specification includes a Sequence Listing.

US 10,280,407 B2

MICROORGANISMS AND METHODS FOR PRODUCING VANILLIN

FIELD OF THE INVENTION

The present invention relates to a genetically modified strain belonging to the order of Actinomycetales, showing an improved production of vanillin made by fermentation of ferulic acid.

BACKGROUND

Vanillin, whose chemical name is 4-hydroxy-3-methoxy-benzaldehyde, is one of the most important aromatic flavor compound used in food, beverages, fragrances and pharmaceuticals. Vanillin was historically extracted from *Vanilla planifolia, Vanilla tahitiensis* and *Vanilla pompona* pods. Today, as a result of constantly rising demand, less than 5% of worldwide vanillin production comes from *vanilla* orchid. Currently, chemical synthesis is the most important process for producing vanillin. However, there is a growing interest in other sources of vanillin and in particular in bio-based routes using bioconversion processes from natural raw material. The use of microbial cells and their enzymes as biocatalysts for the synthesis of chemicals and flavor compounds has attracted much attention lately. Advantageously, the products of such bioconversions are considered as 'natural products' by the European Community Legislation.

Bioconversion processes are based on the following substrates: lignin, phenolic stilbenes, isoeugenol, eugenol, ferulic acid, sugars, aromatic amino acids and waste residues containing these precursors. A recent review (Kaur B, Chakraborty D. "Biotechnological and molecular approaches for vanillin production: a review" Appl Biochem Biotechnol. 2013 February; 169(4):1353-72) lists several biosynthetic pathways and appropriate microorganisms used for biosynthesis of vanilloids.

Strains of the genus *Amycolatopsis* have been identified as being able to synthetize vanillin from ferulic acid, a natural cell wall component of higher plants (U.S. Pat. No. 6,133,003). Among the strains from this genus, the strain accessible under number ATCC 39116 has been selected as being capable of synthetizing large amounts of vanillin, due to its high resistance to vanillin toxicity.

Figure 1:
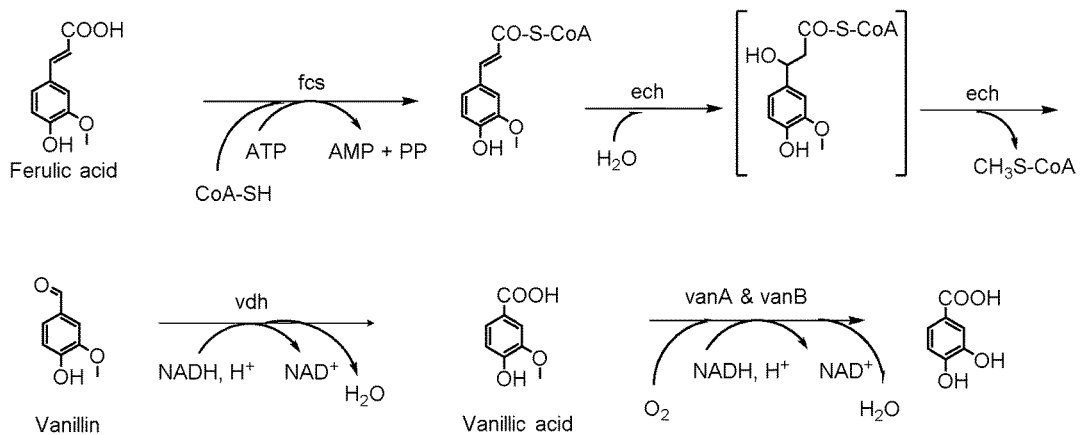
Figure 2:
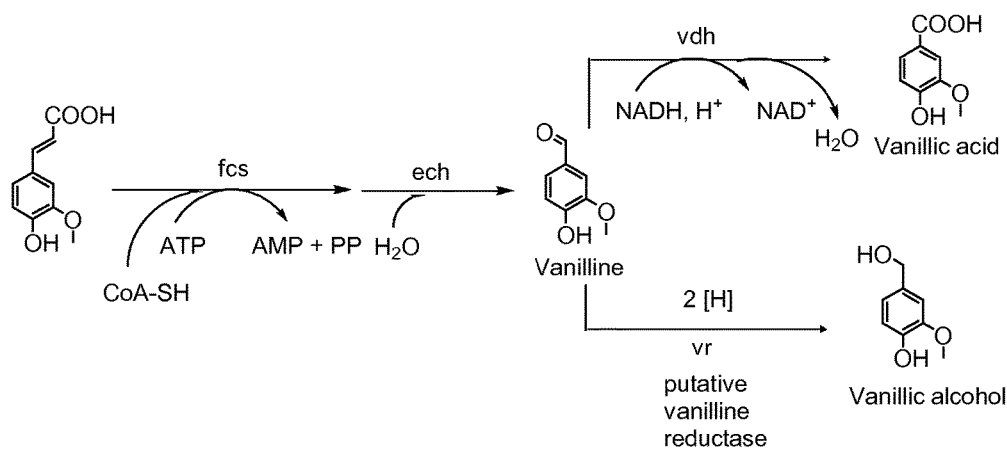

The metabolic pathway of conversion of ferulic acid into vanillin is shown in FIG. 1. In wild-type *Amycolatopsis* strains, the produced vanillin is then converted into both vanillic acid and vanillic alcohol, as shown in FIG. 2. This unwanted consumption of vanillin by endogenous enzymes is a major obstacle for using microorganisms of the Actinomycetales order in an industrialized process for producing vanillin.

In order to prevent the oxidation of vanillin into vanillic acid, the gene coding for the enzyme responsible of this oxidation reaction entitled vanillin dehydrogenase has been recently investigated in *Amycolatopsis* sp. strain ATCC39116. A putative vdh gene was identified, characterized and a vdh deletion mutant was generated. Fermentation of this mutant strain enables the obtaining of a 2.3-fold higher vanillin concentration, compared to fermentation of the wild-type strain, and a substantially reduced amount of vanillic acid was observed (Fleige C, Hansen G, Kroll J and Steinbüchel A, Investigation of the *Amycolatopsis* sp. strain ATCC 39116 vanillin dehydrogenase and its impact on the biotechnical production of vanillin, Appl. Environ. Microbial. 2013, vol. 79, 81; patent application WO 2012/172108). The vdh gene is accessible in NCBI database, under accession number AFY98904.

The conversion of vanillin into vanillic alcohol is catalysed by an enzyme having vanillin reductase activity. However, this enzyme has not been identified yet in a strain of *Amycolatopsis* sp. neither in any strain of the order of Actinomycetales.

BRIEF DESCRIPTION OF THE INVENTION

One of the aim of this study on the vanillin metabolic pathway in *Amycolatopsis* sp. is the identification of one or more enzymes involved in the conversion of vanillin into vanillic alcohol. In particular, one of the goals is the identification of the genes encoding these enzymes, to delete or inactivate said gene(s) in the strain, and therefore to inhibit the catabolism of said vanillin produced from ferulic acid.

Another aim of this study is the identification of recombinant strain(s), in particular of the order of Actinomycetales, presenting a reduced vanillin reduetase activity.

Enzymes potentially involved in the reduction of vanillin include aryl-alcohol dehydrogenases (AAD) that are known to convert aromatic aldehydes into their corresponding alcohols (Gross, G. G. and Zenk, M. H., Reduktionaromatische Säuren zu Aldehyden und Alkoholen im zellfreien System. Reinigung und Eigenschaften von Aryl Alkohol:NADP-Oxidoreductase aus *Neurospora crassa*, Eur. J. Biochem., 1969, vol. 8, 420).

Recently, the complete genome sequence of *Amycolatopsis* sp. strain ATCC39116 was published and the information is accessible in NCBI under accession number J11414689.1, and in Genbank under accession number AFWY00000000 (Davis J. R., Goodwin L. A., Woyke T., Teshima H., Bruce D., Defter C., Tapia R., Han S., Pitluck S., Nolan M., Mikhailova N., Land M. L. and Sello J. K., Genome sequence of *Amycolatopsis* sp. strain ATCC 39116, a plant biomass-degrading actinomycete J. Bacteriology, 2012, vol. 194, 2396). With these data and bioinformatics approaches, it was possible to align the known aad gene sequences from *Saccharomyces cerevisiae*, with the genome of *Amycolatopsis* sp. strain ATCC39116. Classical tools of bioinformatics such as BLAST algorithm (Basic Local Alignment Search Tool) were used to identify similarities between the nucleotide sequences and translate them into protein sequences. Many sequences having similarity with the aldehyde dehydrogenases (ALD) were identified, as well as five protein sequences presenting a high level of identity with the aryl-alcohol dehydrogenases (AAD).

The present invention is in particular related to the identification of enzymes having vanillin reductase activity, and their encoding genes, in a strain belonging to the order of Actinomycetales.

The present invention is also related to a recombinant strain belonging to the order of Actinomycetales, wherein at least one gene encoding an enzyme having vanillin reductase activity is non-functional. In a specific embodiment, the recombinant strain is the strain *Amycolatopsis* sp. accessible under number ATCC 39116.

In a preferred embodiment, the recombinant strain presents a non-functional gene encoding an enzyme having vanillin reductase activity, said gene presenting a sequence having at least 80% of nucleic acid identity with a sequence selected in a group comprising the sequences SEQ ID NO 1, SEQ ID NO 3, SEQ ID NO 5, SEQ ID NO 7, and SEQ ID NO 9.

In another embodiment of the invention, the recombinant strain belonging to the order of Actinomycetales and comprising at least one gene encoding an enzyme having vanillin reductase activity that is non-functional, presents one or more mutations in other genes than the ones presenting a sequence having at least 80% of nucleic acid identity with a sequence selected in a group comprising the sequences SEQ ID NO 1, SEQ ID NO 3, SEQ ID NO 5, SEQ ID NO 7, and SEQ ID NO 9.

In particular, these recombinants strains may present one or more mutations in genes involved in the regulation of the expression of the genes presenting a sequence having at least 80% of nucleic acid identity with a sequence selected in a group comprising the sequences SEQ ID NO 1, SEQ ID NO 3, SEQ ID NO 5, SEQ ID NO 7, and SEQ ID NO 9. Said genes presenting a reduced expression, they are considered as being 'non-functional' in their role of encoding an enzyme having vanillin reductase activity, in the sense of the present invention.

In another preferred embodiment, the recombinant strain additionally presents a non-functional vdh gene encoding an enzyme having vanillin dehydrogenase activity. Thus, this recombinant strain is impaired for both vanillic acid and vanillic alcohol production.

The present invention also relates to a process for producing vanillin or a precursor thereof, comprising the culture of a recombinant strain belonging to the order of Actinomycetales, wherein at least one gene encoding an enzyme having vanillin reductase activity is non-functional in said strain, the culture being performed in an appropriate medium comprising a precursor such as ferulic acid, feruloyl-coenzyme A, caffeic acid, caffeoyl-coenzyme A, p-coumaric acid, p-coumaroyl-coenzyme A, trans-cinnamic acid, trans-cinnamoyl-coenzyme A or phenylalanine, and recovery of the produced vanillin or precursor thereof.

FIGURES

FIG. 1: Schematic representation of the metabolic pathway of ferulic acid conversion into vanillin that is then converted into vanillic acid; the involved enzymes are named as follow: fcs: feruloyl-CoA synthetase; ech: enoyl-CoA hydratase/aldolase; vdh: vanillin dehydrogenase; vanA, vanB: vanillate O-demethylases.

FIG. 2: Schematic representation of the metabolic pathway of the vanillin conversion into vanillic acid and vanillic alcohol. Involved enzymes are named as follow: fcs: feruloyl-CoA synthetase; ech: enoyl-CoA hydratase/aldolase; vdh: vanillin dehydrogenase; vr: enzyme with vanillin reductase activity.

Figure 3:
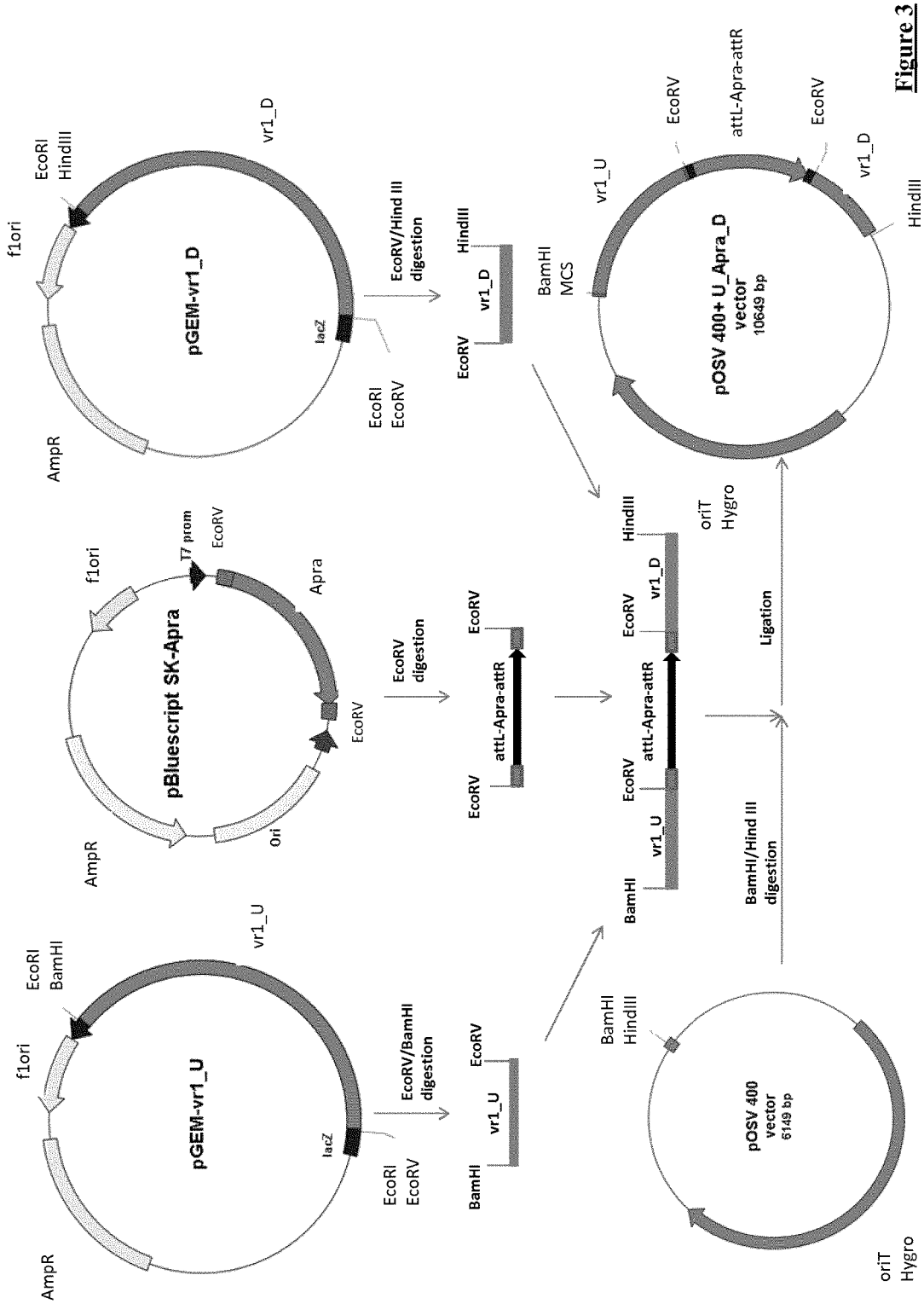

FIG. 3: Construction of the "suicide" plasmid pOSV400+ U_Apra_D; Apra: apramycin resistance gene; att-L: left attachment/excision site; att-R: right attachment/excision site; vr1_U: up-stream region of the gene vr1; vr1_D: down-stream region of the gene vr1.

Figure 4:
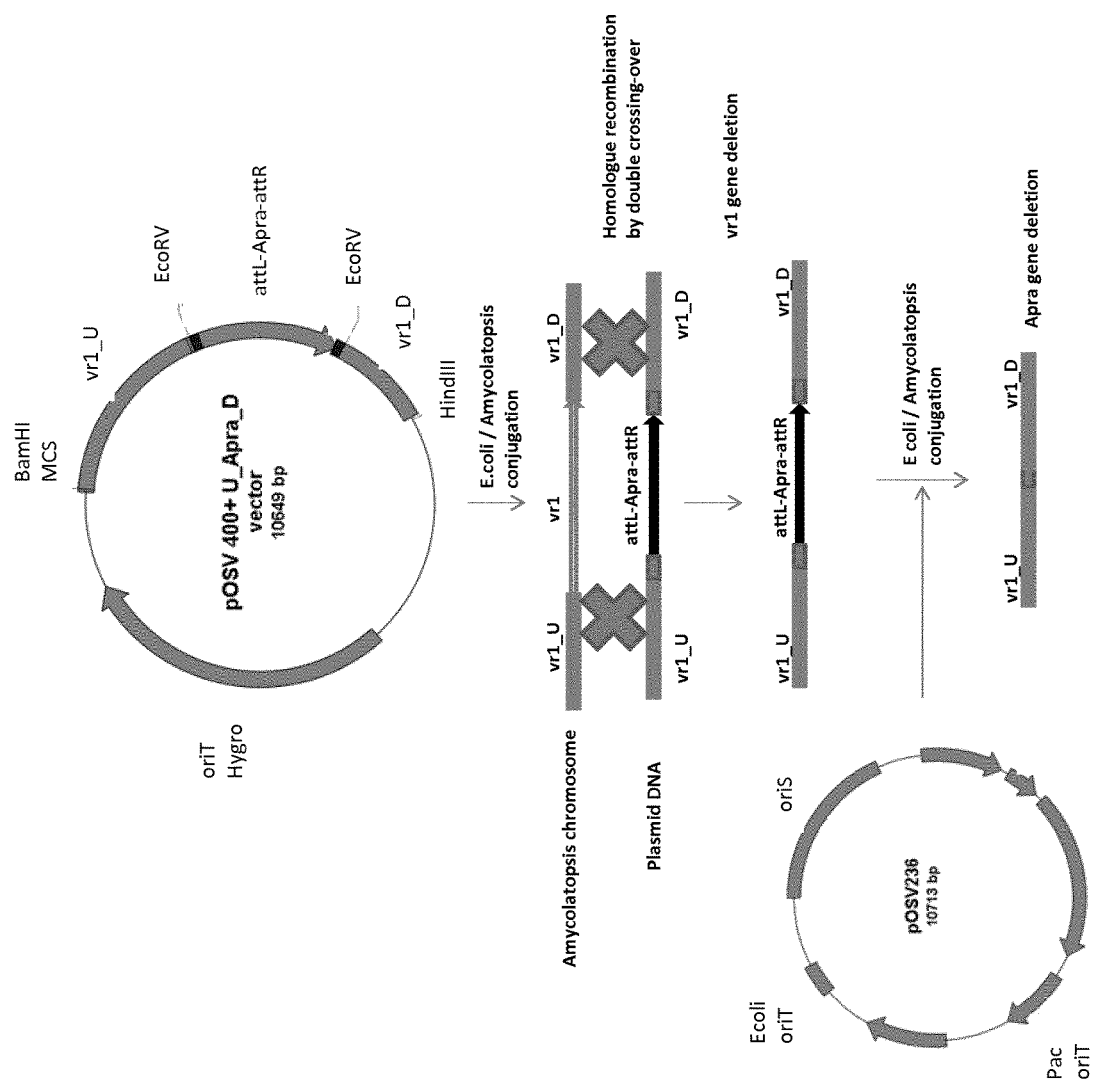

FIG. 4: Use of the plasmid pOSV400+U_Apra_D for conjugation of E. coli/Amycolatopsis sp., and excision of the apramycin resistance cassette; Apra: apramycin resistance gene; att-L: left attachment/excision site; att-R: right attachment/excision site; vr1_U: up-stream region of the gene vr1; vr1 D: down-stream region of the gene vr1.

Figure 5:
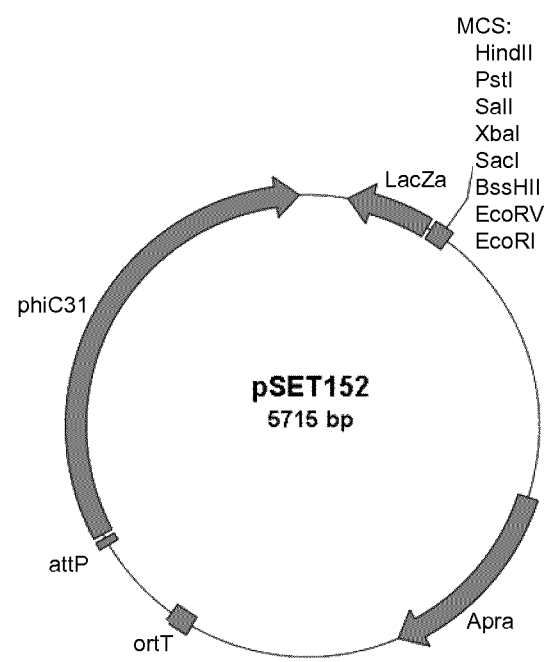

FIG. 5: pSET152 cloning vector used for heterologous expression of vr1, vr2, vr3, vr4 and vr5 genes in Streptomyces lividans; lacZa: β-galactosidase gene for blue-white colony screening; Apra: apramycin resistance gene; phiC31: integrase gene; attP: integration attachment site; MCS: multi-cloning site; ortT: origin of DNA transfer.

DETAILED DESCRIPTION OF THE INVENTION

Inventors have identified enzymes in a strain belonging to the order of Actinomycetales, presenting an enzymatic activity of vanillin reductase, and therefore able to convert vanillin into vanillic alcohol.

A major obstacle for using microorganisms of the Actinomycetales order in an industrialized process for producing vanillin is the presence of endogenous enzyme(s) having vanillin reductase activity. These enzymes catalyse the conversion of vanillin into vanillic alcohol, having the following formula:

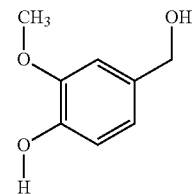

Obviously, this conversion of vanillin into vanillic alcohol reduces the yield of recovered vanillin. To prevent, or at least significantly reduce, the conversion rate of vanillin into vanillic alcohol in producing strains, the present application hereby teaches a new recombinant strain belonging to the order of Actinomycetales having at least one gene encoding an enzyme having vanillin reductase activity that is non-functional.

The following terms are defined for a better understanding of the invention:

A "recombinant strain" or "genetically modified strain" refers to a strain of microorganism whose genetic material has been modified by a non-naturally occurring method, in particular by genetic engineering methods, either by deletion or inactivation of genes, and/or by addition of exogenous genetic material, and/or by random mutagenesis. These methods are well known by the man skilled in the art, and are reviewed in particular in Green & Sambrook, 2012 (Michael R. Green and J. Sambrook in Molecular Cloning: A Laboratory Manual 4$^{th}$ edition (Cold Spring Harbor Laboratory Press, 2012)).

A "genetically modified strain obtained by deletion or inactivation of a gene" refers to a strain whose genetic material has been modified specifically by deletion or inactivation of said gene.

The order of Actinomycetales designates a specific order among Actinobacteria. These bacteria are very diverse and the family contains a variety of subdivisions, as well as yet-unclassified isolates. Most of them are gram positives.

An "enzyme" refers to a protein presenting a catalytic activity in a specific reaction on a specific substrate. Enzymes are highly selective catalysts, which act by accelerating rates of specific metabolic reactions. Enzymes adopt a specific three-dimensional structure, and may employ organic and inorganic cofactors to assist in catalysis.

The "vanillin reductase activity" refers to an enzymatic activity that catalyzes the reaction of reduction, i.e. decrease in oxidation state, of the vanillin. This biochemical reaction leads to the conversion of vanillin into vanillic alcohol, by addition of two hydrogen atoms to the molecule of vanillin (see FIG. 2).

A "non-functional gene" refers to a gene that does not express the expected functional polypeptide, e.g. does not allow the production of the expected active enzyme. In some embodiments, the said gene is not expressed in the recombinant strain, e.g. the said gene is not transcribed or the corresponding transcription product is not translated into a protein, e.g. into an enzyme, having its usual activity. In another embodiment, the coding sequence is partly or completed deleted. In another embodiment, the promoter sequence is deleted. In another embodiment, the gene is inactivated, in particular by introduction of an insert into the coding sequence of said gene.

The statement "at least one gene" refers to the fact that several genes coding for enzymes having vanillin reductase activity can co-exist in a same bacteria. Therefore, the man skilled in the art, in order to obtain a decrease of the activity of "vanillin reductase" in a recombinant strain of Actinomycetales, would inactivate or delete at least one gene, but optionally at least two genes, at least three genes, at least four genes, or at least five genes, in order to obtain a significant decrease of conversion of vanillin into vanillic alcohol.

Strains and Genes

The microorganism of the present invention belongs to the family of Actinomycetales, preferably to a suborder selected from the group consisting of Actinomycineae, Actinopolysporineae, Catenulisporineae, Corynebacterineae, Frankineae, Glycomycineae, Kineosporiineae, Micrococcineae, Micromonosporineae, Propionibacterineae, Pseudonocardineae, Streptomycineae and Streptosporanginea, wherein the suborders of Pseudonocardineae and Streptomycineae are preferred, and even more preferably belongs to the family of Pseudonocardiaceae or Streptomycetaceae, and even more preferably to genus *Amycolatopsis* or *Streptomyces*, and most preferably to the genus *Amycolatopsis*.

In a preferred embodiment of the invention, the recombinant strain is from the genus *Amycolatopsis* or *Streptomyces*.

Among the genus *Amycolatopsis*, the strains *Amycolatopsis* sp. ATCC 39116, HR167 and DSMZ 9992, respectively, are particularly preferred in connection with the present invention. These strains exhibit a very high vanillin tolerance and allow achieving good yields of vanillin by conversion of ferulic acid, even prior to the inactivation or deletion of at least one of the vanillin reductase genes, according to the present invention.

In a preferred embodiment of the invention, the recombinant strain is the strain *Amycolatopsis* sp. accessible under number ATCC 39116.

In microorganisms of genus *Amycolatopsis*, and more particularly in *Amycolatopsis* sp. ATCC 39116, at least one gene coding for an enzyme with vanillin reductase is naturally present. Inactivation or deletion of this gene allows the increase of the yield of vanillin obtainable by conversion of ferulic acid.

Enzymes potentially involved in the reduction of vanillin include aryl-alcohol dehydrogenases. Aryl-alcohol dehydrogenases (EC 1.1.1.91) are enzymes from the oxidoreductases group (EC 1), active on the CH—OH groups (EC 1.1) and with $NAD^+$ or $NADP^+$ as cofactors or acceptors (EC 1.1.1). They are also known as "NADPH-linked benzaldehyde reductase" or "coniferyl alcohol dehydrogenase". The main reaction catalyzed by this enzyme is the oxidation of an aromatic alcohol into the aldehyde in presence of $NADP^+$ as a cofactor. This reaction is reversible and can lead to reductions of aldehydes to alcohols.

In this strain *Amycolatopsis* sp. ATCC 39116, five genes have been identified with putative vanillin reductase activity, as described in example 1. The table 1 below lists five identified sequences in the genome of *Amycolatopsis* sp. ATCC39116. The proteins encoded by genes vr1, vr2, vr3, vr4 and vr5 present high amino acid sequence identity (about 98%) with aldo/keto reductase or oxidoreductase known from the genome of *Amycolatopsis methanolica*.

TABLE 1

Aryl-Alcohol Dehydrogenases identified in *Amycolatopsis* sp. ATCC39116

| NCBI sequence number | Protein size | Molecular Weight | Genome situation | Percentage of identity with known enzymes | Code name and SEQ ID NO. |
|---|---|---|---|---|---|
| ZP_10051335.1 | 320 aa | 34,574 kDa | 3100879-3101841 | Aldo/keto reductase *Amycolatopsis methanolica* (98%) Aldo/keto reductase *Saccharomonospora marina* (62%) | vr1 SEQ ID NO. 1 (gene) and 2 (protein) |
| ZP_10055932.1 | 329 aa | 35,761 kDa | 7961867-7960881 | Aldo/keto reductase *Amycolatopsis methanolica* (97%) Putative oxidoreductase, aryl-alcohol ehydrogenase like protein *Saccharomonospora viridis* (86%) | vr2 SEQ ID NO. 3 (gene) and 4 (protein) |
| ZP_10050304.1 | 320 aa | 33,261 kDA | 2036534-2037493 | Aldo/keto reductase *Amycolatopsis methanolica* (99%) Aldo/keto reductase *Streptomyces* sp. AA4 (81%) | vr3 SEQ ID NO. 5 (gene) and 6 (protein) |
| ZP_10054514.1 | 290 aa | 30,147 kDa | 6462994-6463758 | Oxidoreductase *Amycolatopsis methanolica* (98%) | vr4 SEQ ID NO. 7 |

TABLE 1-continued

Aryl-Alcohol Dehydrogenases identified in *Amycolatopsis* sp. ATCC39116

| NCBI sequence number | Protein size | Molecular Weight | Genome situation | Percentage of identity with known enzymes | Code name and SEQ ID NO. |
|---|---|---|---|---|---|
| | | | | Oxidoreductase *Streptomyces* sp. AA4 (80%) | (gene) and 8 (protein) |
| ZP_10050147.1 | 276 aa | 29,654 kDa | 1886188- 1886991 | Aldo/keto reductase *Amycolatopsis methanolica* (98%) Aldo/keto reductase *Amycolatopsis vancoresmycina* (70%) | vr5 SEQ ID NO. 9 (gene) and 10 (protein) |

The percentage of identity between two amino acid sequences is determined by comparing the two sequences, after optimal alignment using the BLAST algorithm, and determination of the percentage of identical nucleotides/amino acids in the whole length of the sequence. Optimal alignment designates an alignment that can be realized manually, or with the global homology algorithm such as taught by Neddleman and Wunsch (1970).

Inactivation/Deletion of Genes

The man skilled in the art knows different means to obtain non-functional genes in a recombinant strain, such as:
- introduction of a mutation into the gene, in particular generation of a stop codon inducing the expression of a non-functional, truncated protein;
- introduction of an 'insert' into the gene, inactivating its correct transcription; e.g. interruption of the gene sequence by introduction of one or more exogenous nucleic acids, which encompasses introduction of a cassette of exogenous nucleic acid, in particular a cassette encoding an antibiotic resistance gene, or any useful marker;
- replacement of the natural promoter of the gene by a non-functional promoter, or complete or partial suppression of the promoter sequence;
- complete or partial deletion of the coding sequence of the gene;
- random mutagenesis and selection of strains of interest based on adapted screens.

According to a specific embodiment of the invention, in the recombinant strain, at least one endogenous gene encoding an enzyme having vanillin reductase activity has been deleted or inactivated.

Therefore, according to this embodiment of the invention, the recombinant strain is a genetically modified strain obtained by deletion or inactivation of a gene encoding an enzyme having vanillin reductase activity.

A deletion is a mutation in which a sequence of DNA is missing from the wild-type genome. Any number of nucleotides can be deleted, from a single base to an entire piece of chromosome. In a particular embodiment of the invention, deletion of genetic material in the recombinant strain does not cause any frame shift. The man skilled in the art knows different means for deleting specific parts of the genome, in particular coding sequence of genes coding for enzymes with vanillin reductase activity. In a particular embodiment, 100% of the coding sequence of the endogenous gene is deleted. In another embodiment, 90% of the coding sequence of the endogenous gene is deleted. In another embodiment, at least 50% of the coding sequence of the endogenous gene is deleted.

According to a specific embodiment of the invention, in the recombinant 1.5 strain, at least one endogenous gene encoding an enzyme having vanillin reductase activity has been replaced, totally or partially, with a DNA cassette. This replacement is made in particular by homologous recombination. The DNA cassette contains preferentially a marker gene, in particular an antibiotic resistance gene. Preferentially, this mutation does not cause any frame shift.

According to a specific embodiment of the invention, in the recombinant strain, at least one endogenous gene encoding an enzyme having vanillin reductase activity has been inactivated by introduction of a DNA cassette, also called an insert, in particular comprising an antibiotic resistance gene, into said gene.

Preferentially, said DNA cassette is introduced into the coding sequence of the gene. More preferentially, said DNA cassette comprises a stop codon, generating a signal of termination during the transcription process.

Introduction of a DNA cassette into the coding sequence of a gene, even without any removal of said coding sequence, allows the 'inactivation' of the gene, by creating a frame shift and/or by introducing a stop codon. In another embodiment, said insertion of additional nucleotides introduces additional amino acids into the amino acid sequence of the vanillin reductase, preventing the resulting protein from folding correctly.

All genes are surrounded or 'flanked' by regions called "flanking regions". These regions, referred to as the left and right flanking regions, extend for at least 1 to 3 kb on either side (5' and 3') of the genes, and in particular have a length of about 2 kb.

According to a specific embodiment of the invention, the flanking regions of the gene have been amplified, and have been inserted to the DNA cassette used for the genetic modification of the strain, allowing an event of homolgous recombination to occur.

In this specific embodiment, the DNA cassette comprises two sequences (1) and (2), each one having a length of about 2 kb, the sequence (1) presenting at least 90% of sequence identity with the endogenous sequence of the 5' (left) flanking region of said endogenous gene, and the sequence (2) presenting at least 90% of sequence identity with the endogenous sequence of the 3' (right) flanking region of said endogenous gene.

According to the invention, in the DNA cassette used for genetic modification of the strain, the nucleic acid sequence situated between said sequences (1) and (2) does not comprise a functional gene coding for a vanillin reductase.

In a specific embodiment, the sequences (1) and (2) as described above, present in the DNA cassette, presents independently at least 91%, or 92%, or 93%, or 94%, or 95%, or 96%, or 97%, or 98%, or 99%, or 100% of sequence identity with the endogenous sequences of the 5' (left) or 3' (right) flanking regions of said endogenous gene.

According to a specific embodiment of the invention, in the recombinant strain, the previously inserted DNA cassette is removed from the genome of the strain to obtain a marker-less recombinant strain, i.e. a marker-less vanillin reductase knock-out mutant.

In this embodiment, in the recombinant strain, at least one endogenous gene encoding an enzyme having vanillin reductase activity has been inactivated by introduction of a DNA cassette, with or without removal of the coding sequence of the endogenous gene, and then the DNA cassette has been excised.

In this specific embodiment, a small exogenous sequence remains present in the genome of the strain, preferentially comprising from 20 to 100 nucleotides, and more preferably of about 35 nucleotides, this sequence being called hereafter 'the scar'. In a most preferred embodiment of the invention, presence of this scar does not cause any frame shift in the genetically modified strain.

Non-Functional Genes and their Combinations Thereof

The recombinant strain of the invention presents a decrease in vanillin reductase activity, that is due, in a specific embodiment, to the deletion or inactivation of at least one gene coding for an enzyme with vanillin reductase activity.

In said specific embodiment, the recombinant strain is a genetically modified strain obtained by deletion or inactivation of a gene encoding an enzyme having vanillin reductase activity.

In a first aspect of the invention, said at least one gene presents a sequence having at least 80% of nucleic acid identity with a sequence selected in a group comprising the sequences SEQ ID NO 1, SEQ ID NO 3, SEQ ID NO 5, SEQ ID NO 7 and SEQ ID NO 9.

The man skilled in the art will understand that the sentence "a sequence having at least 80% of nucleic acid identity" includes all sequences having 81, 82, 83, 84, 85, 86, 87, 88, 89, 90, 91, 92, 93, 94, 95, 96, 97, 98, 99 and 100% of nucleic acid identity with a sequence selected in a group comprising the sequences SEQ ID NO 1, SEQ ID NO 3, SEQ ID NO 5, SEQ ID NO 7 and SEQ ID NO 9.

Preferentially, said at least one gene presents a sequence having at least 85% of nucleic acid identity with a sequence selected in a group comprising the sequences SEQ ID NO 1, SEQ ID NO 3, SEQ ID NO 5, SEQ ID NO 7 and SEQ ID NO 9. More preferentially, said at least one gene presents a sequence having at least 90% of nucleic acid identity with a sequence selected in a group comprising the sequences SEQ ID NO 1, SEQ ID NO 3, SEQ ID NO 5, SEQ ID NO 7 and SEQ ID NO 9. Even more preferentially, said at least one gene presents a sequence having at least 99% of nucleic acid identity with a sequence selected in a group comprising the sequences SEQ ID NO 1, SEQ ID NO 3, SEQ ID NO 5, SEQ ID NO 7 and SEQ ID NO 9.

The "percentage of identity" between two nucleic acid sequences in the sense of the present invention, is determined by comparing two sequences aligned optimally, through a window of comparison.

Part of the nucleotide sequence in the comparison window may comprise additions or deletions (e.g. "gaps") compared to the reference sequence (which does not include these additions or deletions) to obtain alignment optimum between the two sequences.

The percentage of identity is calculated by determining the number of positions at which an identical nucleic base is observed for the two sequences compared, dividing the number of positions at which there is identity between two nucleotides by the total number of positions in the window of comparison and multiplying the result by one hundred to get the percentage of nucleotide identity between the two sequences them.

Optimal alignment of sequences for comparison can be achieved by computer using known algorithms such as BLAST.

In a second aspect of the invention, said at least one gene encodes an enzyme having vanillin reductase activity, that has an amino acid sequence presenting at least 80% of amino acid identity with a sequence selected in a group comprising the sequences: SEQ ID NO 2, SEQ ID NO 4, SEQ ID NO 6, SEQ ID NO 8 and SEQ ID NO 10.

The man skilled in the art will understand that the phrase "a sequence having at least 80% of amino acid identity" includes all sequences having 81, 82, 83, 84, 85, 86, 87, 88, 89, 90, 91, 92, 93, 94, 95, 96, 97, 98, 99 and 100% of amino acid identity with a sequence selected in a group comprising the sequences: SEQ ID NO 2, SEQ ID NO 4, SEQ ID NO 6, SEQ ID NO 8 and SEQ ID NO 10.

Preferentially, said enzyme has an amino acid sequence presenting at least 85% of amino acid identity with a sequence selected in a group comprising the sequences: SEQ ID NO 2, SEQ ID NO 4, SEQ ID NO 6, SEQ ID NO 8 and SEQ ID NO 10. More preferentially, said enzyme has an amino acid sequence presenting at least 90% of amino acid identity with a sequence selected in a group comprising the sequences: SEQ ID NO 2, SEQ ID NO 4, SEQ ID NO 6, SEQ ID NO 8 and SEQ ID NO 10. Even more preferentially, said enzyme has an amino acid sequence presenting at least 99% of amino acid identity with a sequence selected in a group comprising the sequences: SEQ ID NO 2, SEQ ID NO 4, SEQ ID NO 6, SEQ TD NO 8 and SEQ ID NO 10. In a preferred aspect of the invention, said enzyme has an amino acid sequence presenting 100% of amino acid identity with a sequence selected in a group comprising the sequences: SEQ ID NO 2, SEQ ID NO 4, SEQ ID NO 6, SEQ ID NO 8 and SEQ ID NO 10.

The percentage of amino acid identity is calculated as previously presented for the percentage of nucleic acid identity.

In a specific aspect of the invention, said at least one gene encoding an enzyme having vanillin reductase activity is chosen among the genes:

vr1, presenting the sequence as shown in SEQ ID NO 1,
vr2, presenting the sequence as shown in SEQ ID NO. 3,
vr3, presenting the sequence as shown in SEQ ID NO. 5,
vr4, presenting the sequence as shown in SEQ ID NO. 7 and
vr5, presenting the sequence as shown in SEQ ID NO. 9.

Naturally, it is understood that this gene is non-functional in the recombinant strain according to the invention; therefore the presented sequences are understood as "endogenous sequences before the genetic modification (deletion, inactivation) of said gene".

According to a specific aspect of the invention, in the recombinant strain, at least two genes encoding an enzyme having vanillin reductase activity are non-functional. Preferentially, these genes coding for an enzyme having vanillin reductase activity are chosen among the genes vr1 (SEQ ID NO 1), vr2 (SEQ ID NO 3), vr3 (SEQ ID NO 5), vr4 (SEQ ID NO 7) and vr5 (SEQ ID NO 9).

In a first aspect, two genes encoding an enzyme having vanillin reductase activity are non-functional in the recombinant strain belonging to the order of Actinomycetales.

In a specific embodiment of the invention, the genes vr1 (SEQ ID NO. 1) and vr2 (SEQ ID NO. 3) are non-functional in the recombinant strain.

In another specific embodiment of the invention, the genes vr1 and vr3 (SEQ ID NO. 5) are non-functional in the recombinant strain.

In another specific embodiment of the invention, the genes vr1 and vr4 (SEQ ID NO. 7) are non-functional in the recombinant strain.

In another specific embodiment of the invention, the genes vr1 and vr5 (SEQ ID NO. 9) are non-functional in the recombinant strain.

In another specific embodiment of the invention, the genes vr2 and vr3 are non-functional in the recombinant strain.

In another specific embodiment of the invention, the genes vr2 and vr4 are non-functional in the recombinant strain.

In another specific embodiment of the invention, the genes vr2 and vr5 are non-functional in the recombinant strain.

In another specific embodiment of the invention, the genes vr3 and vr4 are non-functional in the recombinant strain.

In another specific embodiment of the invention, the genes vr3 and vr5 are non-functional in the recombinant strain.

In another specific embodiment of the invention, the genes vr4 and vr5 are non-functional in the recombinant strain.

In a second aspect, three genes encoding an enzyme having vanillin reductase activity are non-functional in the recombinant strain belonging to the order of Actinomycetales.

In a specific embodiment of the invention, the genes vr1, vr2 and vr3 are non-functional in the recombinant strain.

In a specific embodiment of the invention, the genes vr1, vr2 and vr4 are non-functional in the recombinant strain.

In a specific embodiment of the invention, the genes vr1, vr2 and vr5 are non-functional in the recombinant strain.

In a specific embodiment of the invention, the genes vr1, vr3 and vr4 are non-functional in the recombinant strain.

In a specific embodiment of the invention, the genes vr1, vr3 and vr5 are non-functional in the recombinant strain.

In a specific embodiment of the invention, the genes vr1, vr4 and vr5 are non-functional in the recombinant strain.

In a specific embodiment of the invention, the genes vr2, vr3 and vr4 are non-functional in the recombinant strain.

In a specific embodiment of the invention, the genes vr2, vr3 and vr5 are non-functional in the recombinant strain.

In a specific embodiment of the invention, the genes vr2, vr4 and vr5 are non-functional in the recombinant strain.

In a specific embodiment of the invention, the genes vr3, vr4 and vr5 are non-functional in the recombinant strain.

In a third aspect, four genes encoding an enzyme having vanillin reductase activity are non-functional in the recombinant strain belonging to the order of Actinomycetales.

In a specific embodiment of the invention, the genes vr1, vr2, vr3 and vr4 are non-functional in the recombinant strain.

In a specific embodiment of the invention, the genes vr1, vr2, vr3 and vr5 are non-functional in the recombinant strain.

In a specific embodiment of the invention, the genes vr2, vr3, vr4 and vr5 are non-functional in the recombinant strain.

In a fourth aspect, five genes encoding an enzyme having vanillin reductase activity are non-functional in the recombinant strain belonging to the order of Actinomycetales. In particular these five non-functional genes are vr1, vr2, vr3, vr4 and vr5 genes.

In another embodiment of the invention, the recombinant strain of the order of Actinomycetales presenting at least one non-functional gene encoding an enzyme having vanillin reductase activity is obtained by random mutagenesis.

In another aspect of the invention, the recombinant strain may comprise other genetic modifications, in particular genetic modifications improving the production of vanillin. Specifically, the recombinant strain can comprise exogenous genes encoding enzymes involved in the biosynthesis pathway of vanillin from ferulic acid.

In a specific aspect of the invention, in the recombinant strain, at least one gene encoding an enzyme having vanillin dehydrogenase activity is non-functional. Preferentially, this gene is the gene vdh such as described in WO 2012/172108. Deletion or inactivation of said gene is obtained with the same protocols than the ones described previously in this application, for the gene encoding enzyme having vanillin reductase activity.

In particular, at least one of the genes vr1, vr2, vr3, vr4 and vr5, and the gene vdh, are non-functional in a recombinant strain belonging to the order of Actinomycetales.

In a specific aspect of the invention, the gene vr1 and the gene vdh are non-functional in a recombinant strain belonging to the order of Actinomycetales.

In another specific aspect of the invention, the gene vr2 and the gene vdh are non-functional in a recombinant strain belonging to the order of Actinomycetales.

In another specific aspect of the invention, the gene vr3 and the gene vdh are non-functional in a recombinant strain belonging to the order of Actinomycetales.

In another specific aspect of the invention, the gene vr4 and the gene vdh are non-functional in a recombinant strain belonging to the order of Actinomycetales.

In another specific aspect of the invention, the gene vr5 and the gene vdh are non-functional in a recombinant strain belonging to the order of Actinomycetales.

In another specific aspect of the invention, the five genes vr1, vr2, vr3, vr4 and vr5 and the gene vdh are non-functional in a recombinant strain belonging to the order of Actinomycetales.

Process for Producing Vanillin

The invention also related to a process for producing vanillin or a precursor thereof, comprising the culture of a recombinant strain as described above, in an appropriate medium comprising a substrate, and recovery of the produced vanillin.

The following terms are defined for a better understanding of the invention:

The general term "vanilloid" includes vanillin and isovanillin. Chemical structures of vanillin and isovanillin are respectively given here below:

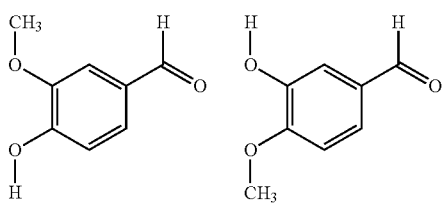

The terms "substrate" and "precursor" as used herein refer to a substrate molecule that is subject to enzymatic reactions in strains of the Actinomycetales order and can be converted into vanillin according to the endogenous biosynthesis pathway. A "substrate" is a precursor or an intermediate in the biosynthesis pathway of vanillin, which is in particular selected from a hydroxybenzaldehyde, or a respective acid, or a respective alcohol or an aromatic amino acid.

This term includes in particular, in a non-limitative manner: ferulic acid, feruloyl-coenzyme A, caffeic acid, caffeoyl-coenzyme A, p-coumaric acid, p-coumaroyl-coenzyme A, trans-cinnamic acid, trans-cinnamoyl-coenzyme A, phenylalanine, tyrosine, protocatechuic aldehyde, 4-hydroxybenzaldehyde, protocacheuic alcohol, 4-hydroxybenzoic acid, 4-hydroxybenzyl alcohol, protocacheuic acid, and combinations thereof.

The terms 'biosynthesis', "bioconversion" 'fermentative production' and 'production' have the same meaning in the sense of the invention, and designates the production of vanillin or a precursor thereof, by a recombinant strain cultivated under appropriate conditions.

According to the invention, the term 'cultivating' is used to denote the growth of bacterial strains.

The term "appropriate medium" designates a medium (e.g., a sterile, liquid media) comprising nutrients essential or beneficial to the maintenance and/or growth of the bacteria, such as carbon sources or carbon substrates, nitrogen sources, urea, ammonium sulfate, ammonium chloride, ammonium nitrate and ammonium phosphate; phosphorus sources; metal salts, for example magnesium salts, cobalt salts and/or manganese salts; as well as growth factors such as amino acids and vitamins. A typical medium is the TSB medium for 'Tryptic soy broth', available from Sigma.

The step of "recovery of the produced vanillin or precursor thereof" will be performed as well known by the man skilled in the art, with techniques such as liquid/liquid extraction, distillation, sublimation, precipitation, crystallization, and pervaporation.

EXAMPLES

Strains, Culture Media, Plasmids and Enzymes

*Escherichia coli* strain DH5alpha is cultured in LB liquid medium (Luria—Bertani, Sigma) at 37° C. with constant stirring (200 rpm/min).

*Amycolatopsis* sp. ATCC39116 is cultured in TSB liquid medium (Tryptic soy broth, Sigma) at 30° C. with constant stirring (200 rpm/min).

The SFM liquid medium (Soya. Flour Mannitol, also called MS medium) contains 20 g/l agar, 20 g/l mannitol and 20 g/l of soybean flour.

Transformation of *E. coli*: 200 ng of plasmids are incorporated into *E. coli* by electroporation (Biorad electroporator) using the following conditions: 200 Ω, 5-2500V for 6 ms in 50 µl. Cells have previously been made competent according to standard protocols.

The plasmids are extracted from the cells of *E. coli* using miniprep kit (Sigma). The total DNA from *Amycolatopsis* sp. is extracted using the Extract—N Plant PCR Kit (Sigma).

Restriction enzymes are commercially available from Fermentas (Thermo Scientific).

Example 1. Functional Characterization of the Proteins Encoded by the Genes vr1, vr2, vr3, vr4 and vr5

To ascertain the enzymatic activity of gene products from vr1, vr2, vr3, vr4 and vr5, these genes were cloned in the cloning site of the pSET152 expression vector (shown in FIG. 5) under the control of the ermE promoter (erythromycin resistance gene).

In particular, the sequence SEQ ID NO 16, corresponding to a BglII_ermE_RBS_vr1_XbaI sequence, was introduced into the pSET152 vector. The coding sequence of vr1 gene is under control of the promoter ermE. The sequence was cloned into the BamHI/XbaI cloning site of pSET152 by added BglII forward primer and XbaI revers primer.

Recombinant plasmids were introduced and heterologously expressed in *Streptomyces lividans*. Recombinant strains of *Streptomyces lividans* were cultivated for 24 hours at 30° C. in a TSB liquid medium comprising 10 mM vanillin; samples of the culture medium were taken regularly during the incubation and analysed by high performance liquid chromatography (HPLC) using a Poroshell 120 EC-C18 column (50 mm×3.0 mm, 2.7 µm particle size). An acetonitrile/water gradient was used as the elution system and a diode array detector was used to detect eluted compounds by their UV spectra at 280 nm and 320 nm. Flow rate was set to 0.6 ml/min and column temperature to 40° C. Under these conditions, the retention times of metabolites were as follows: vanillic alcohol 1.26 min, vanillic acid 2.23 min, vanillin 3.54 min, ferulic acid 5.30 min. All standards were purchased from Sigma Aldrich.

Also, the cell density was checked by OD measurement at 600 nm and was shown to be comparable in all cultures.

Increased concentrations of vanillic alcohol in culture supernatants of *Streptomyces lividans* strains expressing vr1, vr2, vr3, vr4 and vr5 indicate a functional expression of these genes, and the expected enzymatic activity. On the contrary, the negative control, *Streptomyces lividans* transformed with an empty vector, does not show any reduction of vanillin concentration.

Example 2. Construction of a Mutant Strain of *Amycolatopsis* sp. with a Deletion of the Gene vr1

1. Amplification of Left and Right Arms of the Gene vr1

Flanking regions (left and right arms) of the gene vr1 are amplified by adding restriction sites at each end. The whole sequence is represented in SEQ ID NO. 11. To amplify the left arm named vr1_U, of a length of about 2 kb, enzyme restriction sites BamHI are added to the "sense" primer and EcoRV to the "antisense" primer (See table 3, SEQ ID NO. 17/18). The fragment BamHI-vr1_U-EcoRV is thus obtained. For the right arm, the same method allows the obtaining of a fragment EcoRV-vr1_D-HindIII (SEQ ID NO. 19/20). These two fragments are then cloned into the plasmid pGemT easy (Promega) to generate pGEM-vr1_U and pGEM-vr1_D vectors, respectively.

The same protocol is performed for the deletion of each gene. Flanking regions of the genes vr2-vr5 are amplified by adding restriction sites at each end, with the primers listed in table 3 (SEQ ID NO. 21 to 36). The whole sequences of flanking regions and genes are represented in SEQ ID NO. 12, 13, 14 and 15.

TABLE 2

Sequences of genes and flanking regions of said genes

| SEQ ID | Code name |
|---|---|
| 11 | ZP_10051335.1 with flanking regions (vr1 in bold) |
| 12 | ZP_10055932.1 with flanking regions (vr2 in bold) |
| 13 | ZP_10050304.1 with flanking regions (vr3 in bold) |
| 14 | ZP_10054514.1 with flanking regions (vr4 in bold) |
| 15 | ZP_10050147.1 with flanking regions (vr5 in bold) |
| 16 | BglII_ermE_RBS_vr1_XbaI (vr1 in bold, with promoter ermE, RBS sequence and restriction sites) |

TABLE 3

PCR primers used for amplification of adjacent regions of genes vr1 to vr5
Nucleotides underlined and in bold are the site of restriction; other nucleotides are underlined in SEQ ID NO. 11 (vr1), NO. 12 (vr2), NO. 13 (vr3), NO. 14 (vr4) and NO. 15 (vr5).

| SEQ ID | Code name | Oligonucleotide sequence 5'-3' | Oligonucleotide sequence 5'-3' |
|---|---|---|---|
| 17/18 | vr1_U_BamHI/EcoRV | GGATCCCGCGCAGCTCCGGCGATCC | GATATCTGCGGTCCACTTTGTCGGAACGCA |
| 19/20 | vr1_D_EcoRV/Hind3 | GATATCGGCAGCTCGGCGACGGCG | AAGCTTGCGCCAAGGGGCAGCTGCG |
| 21/22 | vr2_U_BamHI/EcoRV | GGATCCGCGGCACACGCCTCGGCGC | GATATCTGTCCGGCAGCCTACCGGAAAT |
| 23/24 | vr2_D_EcoRV/Hind3 | GATATCCGATAGGTTTGGCGCCGTGAC | AAGCTTCGAGCCCGGCGAGGTGACG |
| 25/26 | vr3_U_BamHI/EcoRV | GGATCCCCGAAGTGCTCGTCGGCGATC | GATATCTGCACAGAGAGTAGCTGCGGC |
| 27/28 | vr3_D_EcoRV/Hind3 | GATATCCCGTGGGGTGGATGGCACGT | AAGCTTGCGGTGGCCGTGCCCGCGA |
| 29/30 | vr4_U_Hind3/EcoRV | AAGCTTACGTCAACCGGAACGGGTTGC | GATATCTGGAAATCCCTTCTCGGCTTGTT |
| 31/32 | vr4_D_EcoRV/BamHI | AAGCTTCGCACCACGAGGTGGAGCCCC | GGATCCGGCCACCGACAGGACCGTCA |
| 33/34 | vr5_15_Hind3/EcorV | AAGCTTGCGGCAGATCGAGCAGATCCG | GATATCTCGTCCGCACGTCCCGCCG |
| 35/36 | vr5_D_EcorV/Bgl2 | GATATCAGGCTTCGACTAATCTCAGCGC | AGATCTGTCCGCGTGCGGCTCGTCG |

Sequencing of the two fragments by Sanger (Sequencing Platform DTAMB/Biofidal; UCBL1 Villeurbanne) verifies the absence of mutation in these adjacent areas, and prevents possible problems in the expression of genes adjacent to vr1.

PCR amplification was performed according standard PCR protocols available throughout literature.

2. Construction of the Suicide Vector pOSV400+U_A-pra_D

The vector poSV400_vr1_U_Apra_vr1_D has been constructed as shown in FIG. 4. This vector contains the sequence upstream of the gene vr1 (vr1_U) of about 2 kb, the gene for resistance to apramycin (Apra) and the sequence downstream of the gene vr1 (vr1_D) of about 2 kb.

Each of the BamHI-vr1_U-EcoRV and EcoRV-vr1 D-HindIII fragments was obtained using the restriction enzymes BamH1, HindIII and EcoRV.

The fragment containing the cassette conferring apramycin resistance was obtained from the digestion of the vector pOSV234 with the enzyme EcoRV. The pOSV234 vector has been described by Nguyen et al., 2013 (Nguyen, H. C., Darbon, E., Post-PKS tailoring steps of the spiramycin macrolactone ring in *Streptomyces ambofaciens*, Antimicrob. Agents Chemother., 2013, vol. 57, 3836). This cassette is flanked by the attL and attR integration sites that are used in the last step to excise the apramycin cassette. This gives the EcoRV-apra-attL+R-EcoRV fragment. This fragment is ligated with the vr1_D and vr1_U fragments, and the whole is inserted by ligation into the pOSV400 vector, previously digested with the enzymes BamHI and HindIII. This vector pOSV400 carries a hygromycin resistance cassette and an origin of transfer oriT, essential for the transfer of the vector in the inter-species conjugation. This plasmid also carries a replication origin (ori) functional in *Escherichia coli* only. This vector is therefore a 'suicide vector' which is not capable of replicating in *Amycolatopsis*. Consequently, only its integration into the genome by homologous recombination will be possible.

The ligation is performed according to the conditions indicated by Fermentas.

3. Conjugation *E. coli/Amycolatopsis*

The obtained vector is transformed into a strain of *Escherichia coli* capable of cross-species conjugation, and methylation deficient (ET12567 strain whose genotype is dam-dcm-lisdS as described by MacNeil et al. (MacNeil, D.

J., Occi, J. L., Gewain, K. M., MacNeil, T., Gibbons, P. H., Ruby, C. L., Danis, Si., Complex organization of the *Streptomyces avermitilis* genes encoding the avermecitin polyketide synthase, Gene, 1992, vol. 115, 119)). The conjugation between this strain of *E. coli* and *Amycolatopsis* sp. is realized by mixing *E. coli* and a suspension of *Amycolatopsis* sp. spores. The spores were prepared as described by Kieser et al. (Kieser, T., Bibb, Mi., Chater, K., Hopwood, D. A., Practical *Streptomyces* genetics, 2000, The John Innes Foundation, Norwich (ISBN 0-7084-0623-8)). The double recombination of the vr1 gene flanking regions allows the exchange of the vr1 gene with the apramycin cassette. The conjugants are then selected with their ability to resist to apramycin. The *E. coli* colonies are eliminated by the addition of nalidixic acid. This antibiotic is added in an overcoat layer of SNA medium (Bacto Nutrient Broth and agar).

4. Excision of the Apramycin Cassette

The pOSV236 vector is introduced in *Amycolatopsis* strain by conjugation. This vector carries a gene encoding an excisase, also called exeisionase, and a gene encoding an integrase. The excisase is encoded by xis gene and the integrase is encoded by the int gene respectively. The integrase promotes the intermolecular recombination between the att sequences required for site-specific recombination. Thus, the expression of both int and xis leads to the specific recombination between the attL and attR sites and thus to the excision of the cassette introduced into the genome of the strain. The introduction of this plasmid is validated by obtaining conjugants resistant to thiostrepton. These conjugants are also spread on TSB agar medium, supplemented with apramycin, to identify those who have lost this specific resistance. These strains are cured of the vector pOSV236 after several subcultures.

5. Analysis of the Scar on the *Amycolatopsis* Genome

*Amycolatopsis* strains with the vr1 deleted, and replaced with a small 'scar' comprising 35 nucleotides, are finally obtained. Using primers, listed in table 2 specific for both ends of the scar, the region was amplified and then sequenced.

Example 3. Production of Vanillin with Wild Type and Recombinant Strains of *Amycolatopsis* sp. ATCC 39116

The wild-type strain ATCC 39116, and recombinant strains Δvr1 and Δvr1Δvr2Δvr3Δvr4Δvr5 such as obtained in previous examples, were cultured for 24 h in parallel under the same conditions, in a TSB medium at 30° C., pH 7 and under constant agitation. Obtained pre-cultures were diluted with fresh medium, and cultured until carbon source was depleted. Then ferulic acid was added to 10 mM final concentration. Produced vanillin and metabolites were followed and quantified by high performance liquid chromatography (HPLC).

At the step "24 h of culture", the level of vanillin produced by fermentation of the recombinant strains was significantly superior to the level obtained with the wild-type strain, cultivated under the same conditions, as indicated in the table 4. No vanillin reduction into vanillic alcohol is detectable in HPLC chromatograms.

TABLE 4

Production of vanillin and vanillic alcohol by fermentation of wild type and recombinant strains

| Strain | Vanillin amount | Vanillic alcohol amount |
| --- | --- | --- |
| Wild type ATCC 39116 | +++ | ++ |
| Δvr1 | ++++ | −/+ |
| Δvr1Δvr2Δvr3Δvr4Δvr5 | +++++ | --- |

SEQUENCES 1-16

SEQ ID NO. 1: coding sequence of the gene vr1
atgagataccggcttttcgggcgcaccgggctgcgcgtggcggagatgttcctcggggcg
atggcgctgcaggaaccggacgaggcgaggcgggtggtcaaggcctacgccgacgccggg
ggcaacgtgatcgacacggcctcggcgtacgcggagagcgagaacgtgctgggcgaggtg
ctgaccgaccgcgaccggttcgtgctggccaccaagtacacgctgacgcgggatccgcac
gacccgaacgccgggggcagccaccgcaagaacctggtcgcgtccctggagcgcagcctg
cggcggctgcgcaccgactacgtcgacatcctgtgggtgcacacgtgggacccgcacacg
ccggtcgccgagacgctgcgtgcgctggacgacctggtgcgggccgggaaggtcaggtac
ctcggggtgtccgacacgcccgcgtgggtggtgagcgggccgacgtgctggcggagtgg
cgcgggtggacgccgttcgccggggtgcaggtgccctacagcctgctgaaccgcgacatc
gagcgcgacgtgctgaccgatggccgacagctggggctgaccgtcgcggcgtggggcgtc
ctggagcacggcgcgctgaccgggtccagccgggtcggttcgccgtcgccggagcagcag
cgggtggcggcggcggtgcgcgcggtggcggacgagctgggtgtcacgccggcacaggtg
gcgatcgcgtggtcgcgggcgcggtcggcggtcgtgcacccgctgatcgggttccggacg
gcggacccgggtcgcggagagcgtcgccgccctggacgtgacgctgccccccggaagcggtg
gcgaagctggaggcggccggcgccgttcgagccgggcccgttcgccgacttcgtgaaccag
tcggcggccagcgccggggtgttcggccacggcgaggtggtggcgcgtcagctgagggag
tga SEQ ID NO. 2: protein encoded by vr 1
MRYRLFGRTGLRVAEMFLGAMALQEPDEARRVVKAYADAGGNVIDTASAYAESENVLGEV
LTDRDRFVLATKYTLTRDPHDPNAGGSHRKNLVASLERSLRRLRTDYVDILWVHTWDPHT
PVAETLRALDDLVRAGKVRYLGVSDTPAWVSRADVLAEWRGWTPFAGVQVPYSLLNRDI
ERDVLPMAEQLGLTVAAWGVLEHGALTGSSRVGSPSPEQQRVAAAVRAVADELGVTPAQV
AIAWSRARSAVVHPLIGERTADRVAESVAALDVTLPPEAVAKLEAAAPFEPGPFADFVNQ
SAASAGVFGHGEVVARQLRE SEQ ID NO. 3: coding sequence of the gene vr2
atggagtttcgccgtctcggccgcagtggcctgtccgtcagtgagatcgcctacgggaac
tggctcacccacggttcccagatcgacgaggaccaggcccaggcctgcatcaaggccgcg
ctcgacgcgggcatcacgaccttcgacaccgccgacgtctacgccaacacccctggcggag
tcggtgatcggccgcggtctggccggtcagcgccgggagagcctggagatctgcacgaag
gtgttctggccgaccggccccggcggcccgaacgaccgcgggctggccgcaagcacatc

SEQUENCES 1-16 atcgagtcctgccacgcctcgctgaagcggctgcagaccgaccacatcgacctctaccag
gcgcaccggttcgaccgaccgtgccgctggaggagaccatgtcggccttcgccgacctg
gtccgccagggcaaggtgctctacatcggggtgtcggagtggaacgccgaggagatcacc
cgcggcgccgcgctggcccgcgagctgcggatccccttcgtgtcgaaccagccgcagtac
aacatgctctggcgcgtcatcgaggcgaggtcgtgcccgccagcgagcgcgaggggctg
agccagatcgtctggtcgccgatcgcgcagggggtgctgaccggcaagtacaagccgggt
cagccgccgcccgcgggtcgcgcgccacggacgagcggggctcgcagttcgtgcagcgg
ttcctgcgggacgaggtgctcgagcgcgtggcccggctggagcgcgctggccgcgcaggcg
gggctgacgctggcgcagctggcggtggcgtgggtgctgcagaacccgaacgtcgcctcc
gcgatcgtcggcgcgtcgcggccgagcaggtgcacgagaacgtgaaggcggcgggcgtg
aagctcgacgccgacctgctgaccgagatcgactcggtgctgctgggcgtggtcgaggac
gatccgcgcctgaccgctcgcgccggctga SEQ ID NO. 4: protein encoded by vr2
MEFRRLGRSGLSVSEIAYGNWLTHGSQIDEDQAQACIKAALDAGITTFDTADVYANTLAE
SVLGRGLAGQRRESLEICTKVFWPTGPGGPNDRGLGRKHIIESCHASLKRLQTDHIDLYQ
AHRFDPTVPLEETMSAFADLVRQGKVLYIGVSEWNAEEITRGAALARELRIPFVSNQPQY
NMLWRVIEAQVVPASEREGLSQIVWSPIAQGVLTGKYKPGQPPPAGSRATDERGSQFVQR
FLRDEVLERVARLEPLAAQAGLTLAQLAVAWVLQNPNVASAIVGASRPEQVHENVKAAGV
KLDADLLTEIDSVLLGVVEDDPRLTARAG SEQ ID NO. 5: coding sequence of the gene vr3
atgcagaagcgacagctgggcaggtcggggttgcgggtctcccggatggcgctcggcacg
atgtcctggggcgcggagaccgacgccgacgaggcggccagccagctcgtcgcgttcgtc
gaggcgggcgggacgctcgtggacaccgccgacatctactccggcggcgagagcgagcgg
atcctcgggggcctgctgggcgacctggtgccgcgtgacgagatcgtcgtggcgaccaag
gccgtcgcccggcgcaccgacgggccgttcggcggggcgcctcccgcggcgcgttgttg
tccgcgttggagggtcgctgcggcggctcggcgtggaccacctgaccgtggcagctg
cacgcgtgggacgactcggtgccgctggaagagacgctgtcggcgctggaccacgcggtg
acctcgggcaaggtccgctacaccggggtgcaactacgcgggctggcagctggcctcg
gccgcggcggcccggcaggccgggctggtcgccacgcaggccgagtactcgctggtggag
cgcggggtggagcgcgagctggtcccggcggcccgccaccacgggctcggcgtgctgccg
tgggcgccgctgggccgcggggtgctgaccggcaagtaccgccacggcacgccggccgac
tcgcggggcgcgtcggccgagtacgccggctacgtcgagcagcaccgcaccgagcgggcg
gcgcggatcgtcgaggcggtcgccaccgcggccgacgggctgggggtgtcgccgctggtg
gtggcgctggcgtgggtgcgggaccggccgggcgtggtcgcgccggtggtcggggcgcgc
gacaccgggcagctgaccgggtcgctggccggcggaggagatcgccctgccggtcgcgatc
tcctcggcgctggacgacgtcagcgcggtcgagttcggttaccccgagcggggcacgaag
tga SEQ ID NO. 6: protein encoded by vr3
MQKRQLGRSGLRVSRMALGTMSWGAETDADEAASQLVAFVEAGGTLVDTADIYSGGESER
ILGGLLGDLVPRDEIVVATKAVARRTDGPFGGGASRGALLSALEGSLRRLGVDHLDLWQL
HAWDDSVPLEETLSALDHAVTSGKVRYTGVCNYAGWQLASAAAARPAGLVATQAEYSLVE
RGVERELVPAARHHGLGVLPWAPLGRGVLTGKYRHGTPADSRGASAEYAGYVEQHRTERA
ARIVEAVATAADGLGVSPLVVALAWVRDRPGVVAPVVGARDTGQLTGSLAAEEIALPVAI
SSALDDVSAVEFGYPERGTK SEQ ID NO. 7: coding sequence of the gene vr4
atgacagcgaacacactggccggcggcaccttcaccctcgcaggcgggctcaccgtcggg
cgcatgggctacggcgcgatgcagctggccgggcctggcgtgttcgggccgcccgcggac
cgggacgccgcggtcgcggtcctgcgcgaagcggtcgagctgggtgtcaaccacatcgac
accgccgacttctacgggccgcacgtgacgaaccagatcatccgcgaggcgctgcacccc
tacgacgggatcgtggtggtgaccaaggtcggcgcggtgcgcgacgaccagggcgcctgg
gtgcaccagcgatcgccggagcagctgcgtgcccaggtcacgacaacctgcgcaacctc
ggcgtcgacgcgctcgacgtggtcaacctgcgcgtcggcggcggggacgacggccactcc
gcggtgcccggctcgatcgccgagccgttcaccgcgctggtcgagatgcagcaggagggg
ctgatcaagcaccctcggcatcagcacggtcaacgccgagcaggtcgccgaggcgcagtcg
atcgcgccggtcgtgtgcgtgcagaacgcctacaacgtggcccaccgcgaggacgacaag
ctggtcgagtcgctggccgcgcagggcatcgcgtacgtgccgtacttcccgctcggcggg
ttctcgccgctgcagtcggaggtgctgaactcggtggccgcccgcctcggcgcgaccccg
atggccgtcgcgctggcctggctgctgcagcggtcgccgaacatcctgctcatcccgggc
acgtcgtcggtcgcccacctgcgcggagaacgtggccgccgcgtccctggacctccccgcg
gacgcgatcgccgaactcgacgcgatcgcctaa SEQ ID NO. 8: protein encoded by vr4
MTANTLAGGTFTLAGGLTVGRMGYGAMQLAGPGVFGPPADRDAAVAVLREAVELGVNHID
TADFYGPHVTNQIIREALHPYDGIVVVTKVGAVRDDQGAWVHQRSPEQLRAQVHDNLRNL
GVDALDVVNLRVGGGDDGHSAVPGSIAEPFTALVEMQQEGLIKHLGISTVNAEQVAEAQS
IAPVVCVQNAYNVAHREDDKLVESLAAQGIAYVPYFPLGGFSPLQSEVLNSVAARLGATP
MAVALAWLLQRSPNILLIPGTSSVAHLRENVAAASLDLPADAIAELDAIA SEQ ID NO. 9: coding sequence of the gene vr5
atgcgcgaggcgacgttcgcggtgctcgacgcggcgtacgcggccggtgtgcgctggatc
gacgtcgcccgctcctacggccggccgaggagttcctggccgggtggctggccgagcgc
ggccacggcgacctcaccgtgtccagcaagtgggctacacctacgtcggcggctggcgc
atggacgccaccatgcacgaggtgaaggagcactcggcgggcgtgttctcccgccagtgg

SEQUENCES 1-16 accgaaagccgctcgctgctcggcaacgccatcaacctctaccaggtgcactcgctcacc
gtggacagcccgttgttcaccgacgaggcgctgcagcgggcgctggcggcgctcagcgac
gacggcgtgcgcgtcgggttctccacttccgggccgaagcaggcggaggtgatccggcgg
gcgttcgagctggaagtggccgggcggccggtgttctcggccgtgcagtcgacctggaac
ctgctcgaaccgtcggcaggcccggcgctcgcggaggcgcacgcggccgggaacctggtg
ctggtcaaggaaaccctcgccaacggcaggctggtggtcaacccgccgccccgcgatcacc
cgcctggcgcaacgctacgcagtcggcgccgacgcggtggcgatcgcggcggtgctcgcc
cagccgtgggcggacacggtcctcatcggcccgtccagcccgcagcagctggccgccaac
ctcgccgcgaacggcgtcgacctgccacggggcgaactcgccggcgctgcgggcgctggcc
gagccgccggaacggtactgggatcggcgatcctcgctgcagtggcagtga SEQ ID NO. 10: protein encoded by vr5
MREATFAVLDAAYAAGVRWIDVARSYGRAEEFLAGWLAERGHGDLTVSSKWGYTYVGGWR
MDATMHEVKEHSAGVFSRQWTESRSLLGNAINLYQVHSLTVDSPLFTDEALQRALAALSD
DGVRVGFSTSGPKQAEVIRRAFELEVAGRPVFSAVQSTWNLLEPSAGPALAEAHAAGNLV
LVKETLANGRLVVNPPPAITRLAQRYAVGADAVAIAAVLAQPWADTVLIGPSSPQQLAAN
LAANGVDLPRGELAALRALAEPPERYWDRRSSLQWQ SEQ ID NO. 11: Sequence 5'-3' of ZP_10051335.1: coding sequence
of vr1 gene is in bold, the primers used for the amplification
of the flanking regions vr1_U and vr1_D are underlined.
<u>cgcgcagctccggcgatcc</u>gttgcggtaggccaggatgatcgggaacagcgccaggcagg
tcgcgccggtcagcagcgggtagccgatcggcggcgggatgatcgccagcggcgtgaaca
gcaccgcggagaacggcgggtaggtgtagggcagcgcgccgatggtcgagacgggca
gctccgagtagatcgagtggcccttgaggaacgtgtccgcgcccagccggtagatgtcga
cgtcggtcggccacttccggatgccgtgcgcgtagtacgcgagcgcggcgaacaggccga
cggccagcaggagttccaagcccaggcgtacccgctcggcggtactgccgtacctcatcg
tctcgatgacagatttcactcgttctcccagtcccggccaggcgtgatctcacggaacag
acgccgcaacgcctatcttcgttgcccgcgtgatcgatgttacgagcgggtccccttgc
gctacgcgcggctgcggtcggtgaacacgatccagcgaagcacgctgtagaggaacaccg
catccaacgcgccggcgatgatgcgcgccaggtggtactgcacgcccagcgcggccaggc
cggcccggcgcgaggatgaacgcgaagtagttgaccgccaccgcgatcgcgtagagca
cggcctgccgcccgaccggagcgtgcgagcgaagttgaagacgcggttgagcacgaagc
tcagcgcgaaggcgcagacgtaggccacggtgatggcgaccggcagcggcagcccggcca
cgccgtggcccaggtcagcagcagcaggtcgacgccgaaggtgaacccgttgatcagcg
cgaagcccacgaagctgggcgggaccagcgtgttcagcccgaagggcaggtaccggacga
ccgtcgcgcagaacgacgcgaacctctccacgagcgaccgctcacccggatgtcctgtt
gcacggcgccacgtggcagaaccgggtgacgggaaggtgagcagccggtagtcaacagg
cggcggaaagtgtcaccgaccccacggagatcacacttcgggctgatatcttcttgtgac
cccgtccgtgtgatcctccgtccccgcggaggcgcgcgccgccccgaagcccccgtca
ggaggcgcggatgttcgcctggttctgggtgacgctcggcgtcgccttcggctcggcgat
cgtgcccgtgatcagcgtcgaggtgttcgtgctggggctcgtggccagcgagccggggct
gcactggctgctgatcggcgcggccgtctcgatcggccagatcgccggcaaactgctgta
ctacctggccgcgcgcggatcgatcaggctgccgcggttcctgcacgaccgcctgcaccg
ggagcgcccgcccagccgccgccgcgaccggtggcaccaaagtggctgcgcgg
caaggtggaggccctgcgcgagcgctgccaccggcacccgcactggatgacgggaccta
cggggtcagctcgctgatcgggctcccccccgttcatggcgacgaccgtgctggcgggcct
ggccgacatgcggatgtcgacgttcctcacggcgggcctgaccgggcggttcatcaggta
cagcgcgctggccgcgtgcccggcggtgttcgcgggatggttccaccactgagctcgggc
taccggaggagccggaacagcccgtcggaggggtccaccacgacggcgaggattcgccg
gccgtcgggacccggtggctgggcccgcgtgggtcacctcgtgtcggtctgcccgccgg
tctcgcacggcgggcgcagacgaccagcgcggtcgcgggccggccgccgcttaccccggg
caccggccctacggcacgacctcgtcgaagttcccggcggaggcgggttgcgaccggccg
cgagtgagtttggcgccacacgtgccggaggcggc<u>tgcgttccgacaaagtggaccgc</u>**at
gagataccggcttttcgggcgcaccgggctgcgcgtggcggagatgttcctcggggcgat
ggcgctgcaggaaccggacgaggcgcggcgggtggtcaaggcctacgccgacgccggggg
caacgtgatcgacacgctcggcgtacgcggagagcgagaacgtgctgggcgaggtgct
gaccgaccgcgaccggttcgtgctggccaccaagtacacgctgacgcgggatccgcacga
cccgaacgccggggggcagccaccgcaagaacctggtcgcgtccctggagcgcagcctgcg
gcggctgcgcaccgactacgtcgacatcctgtgggtgcacacgtgggacccgcacacgcc
ggtcgccgagacgctgcgtgcgctggacgacctggtgcgggccgggaaggtcaggtacct
cggggtgtccgacacgcccgcgtgggtgvtgagccgggccgagctgtggcggagtgccg
cgggtggacgccgttcgccggggtgcaggtgcccacagcctgctgaaccgcgacatcga
gcgcgacgtgctgccgatggccgagcagctggggctgaccgtcgcggcgtggggcgtcct
ggagcacggcgcgctgaccgggtccagccgggtcggttcgccgtcgccgagcagcagcg
ggtggcggcggcggtgcgcgcggtggcggacgagctgggtgtcacgccggcacaggtggc
gatcgcggttcgcggggcggtcggcggtcgtgcacccgctgatcggttccggacggc
ggaccgggtcgcggagagcgtcgccgccctcgacgtgacgctgccccggaagcggtggc
gaagctggaggcggcggcgccgttcgagccgggcccgttcgccgacttcgtgaaccagtc
ggcggccagcgccggggtgttcggccacggcgaggtggtggcgcgtcagctgcgggagtg
a<u>ggcagctcggcgacgcggc</u>gacggtccagtgcgccggtttcggcgcctcgccgggcgg
cagggcccaggatccaggtcagcacggccgatgccttggcgtgggtgccgagcagtcccca
ctggttgaggcggacaccggcgtccgcctcgtagccgtggcacagccacgagtgcacgtc
catcaggtcgaagtccgcgccgatgatctcgaagccacgcaggacggcgcgctccggcat
cggcgcttgctgtaggagttgggcagcgcttccgccttggccgggtccagctcgccgcg
gaccgcctcgacgagcgccggcgtcgcggcgggtgaagccgatcgccagcaggtgccc
gtcgaaccgcgccgccgcggccgggtcggcgtgccaggcccagaactccgggccgtggtc

SEQUENCES 1-16 gacaccggtgaggcacctgctcaggctgatgaacgactccggcaaccaccgcgattgcca
cccttcccgcgcgggacgcgggacggccaggtagcccgcgagcaggagttcgtcgtccac
ccgcacagtgtcgcagcgcccgcaccgggttcgcgacggattaaggatcagcgcccgggg
gtcccggttctctggcggttgccatccaccggtcggcgagcgtgccgcgctgcgcgaac
cgcctcgggcgtgggttcgcgttgcgcgtgcgccaaccggcaccgccgcagtcctccga
gtgcacgcaccgcgggcgcggcaccacctaacgcgcggcctccgccgcttccaggtccag
cgccttgcgcatcgtggcgcgggcgcggcgccggtcgcccgccaggtcgtacgcgtgcgc
caaccggtaccagtaccgccagtcctcggggtgctgctccagctccgcgcggcgctcctc
gaaccacgcgtccgccggcgcggtccaccgcggccggacgggcggcgcggcaggtcgtc
gacgtccggcagcccgccctcggcgtccagccgtcgcgccaggtgctggatccgcgtgcc
ggaccgccaggtggcgacgaccatccacagccccagcagcggcagcacgagcacgccgac
accgagcgcgatgcccacgccggtgccggtcgcgatcagctccaccccgcgccccgag
cagcaccaggtagaccaccagcgcggcggtcatccagtgcgacgttgcgggccttcac
aggtcgagcacgttctcgaggccgacggtcaggccgggacggccagcacctcccgcacc
ccgagcagcacaccgggcatgaacgaggtccggtccatcgagtcgtgccggatggtgagc
gtctcgccctcctggccgaacaggatctcctcgtgcgccaccagcccgggcagccgcacc
gagtgcacgtgcacgtcctcgacccgcgcgccgggcgccgtccagttcgctcgtcgtc
gcgtccgcgcccggcttcagcccgcctcgcggcgcgcctccgagatcagccgcgccgtg
tgggccgccgtgccggacggggcgtccgccttgcggttgtggtgcagctcgatgacctcg
accgactcgtagaaccgggccgcctgctgcgcgaaccgcatcgcgagcaccgccgcgagc
gcaaagttcggcgcgatcagcaccccgacctccggcttgcccgccagccacgagcgcacc
gtctccagccgctcctcgctgaacccggtggtgccgacgaccgcgtgcaacccgttgccc
accaggaactccaggttgcccatcaccgcgtccgggtgggtgaagtcgacgaccacctcc
gcgccggcctcggtcagcgcggtcaggtcgtcgcccgcgtccagcttcgccacgaccgtc
atgtcgggcgcgccccccggcggccttgaccacctgcgcacccatccgtccctgggcgcc
agcacgccgacccggatcgggttgtcctcgccgcgggggttcatttcgcgatcacctcgt
gcagatcttccggtaggtcctgctcggaagcgtacggcccgaccaccgcggcggcggtga
ccctcccggcgtcccgaacagggtgcgggccagatcacacacctcctcggtggtcaccg
cggcgatccgctccaccgactcgtcgacggtgaggtgcacgccgtagttgagctcctgct
tgccgatcgcgcgacatccgcgacgcggtgtcctccaggcccagcacgatcccgccgcgca
gctgccccttggcgc SEQ ID NO. 12: Sequence 5'-3' of ZP_10055932.1: coding sequence
of vr2 gene is in bold, the primers used for the amplification
of the flanking regions vr2_U and vr2_D are underligned.

gcggcacacgcctcggcgcccggccgcctgcgcc

SEQUENCES 1-16 ccgcgctgggtgagctggaggcgctcggcgcgtgggtcgcggcctgccagggctcggcgc
cgccgcggcggttccagcggccccgggtgatcgtgttcgccggggaccacgggatcgccg
cgaagggcgtctccgcctaccggccggaggtcaccgggcagctggtggacagcctgctca
agggcgccgggccggtcgcggtcgccgccgcggtggccgacgccgggctgcgcgtggtgg
acatcgcggtggacgaggagacgccggtcgccgagtacaaggtccgggcgggctccgggt
cgatcgacgtcgaggacgccctcaccgacgacgaggtgcgggccgccctgcgggccggca
tggcgatcgcggacgccgaggtggacgagggcgccgatctgctggtcgcggggcagcgtcg
gggtcggggcgaccacaccggccgcggtgctggtcgccgcgctgaccggcgccgagccgg
tggccgtggtcggccgcggttcgggcatcgacgacaacgcgtggatgcgcaagaccgtcg
cgatccgggacgcgctgcggcgggcccgggcggtgctgcccgacccggtggcgctcctgc
ggaccgcgggtggcgcggacctggccgcgttgacccgggttcctggcgcaggccgcggtcc
gccgcaccccggtgctgctggacgggctcgcggtcggcgcgggcggcgctggtggcggagg
aactggcgcccggcgcgcgctcctggtggcaggccgcgcaccgcgacgccgagccggagc
accagatggtgctggagcacctcgacctcaagccggtcgtcgacctgggcatccgcctcg
gcgacggcaccggcgccgcgacggccctcccgctgctgatcacggccgcccggctgctca
cggacctgccgacgcacgcggaagccggggtcacgccgccgaacgcttgatcctgacgcg
acgtcaggtcctagcgtcgtccacaccggcgcaaaagcgctggtggaagtgggtgaacgg
catgttctacaaggtcggcgagctggcacgggcgaccggtctgacggtgcggacgctgca
ccactacgaccacgtgggtctcgtgcgcccgtccgggcggacgcactccgggcaccggct
ctacgacgagtccgacgtccggcggttgtacgaggtgctggccctgcggcagctgggcct
gccgctcgaggacatcggcgcggcctggagggcacgtccgacctggccgagctgctcac
gcggcaccgggaccacctcgaccggcagctggtggcgatgcgcacgctccgcgcgcacct
caccacgatgctggcggccgtcgacgaaccggcaggcgtcaccggcttcctggctctgat
ccgggaggtgaccaccgtgcagcgagacggtgaagcagtacttcagcgaaacccagctggc
ggagctggccgagcgccgatcgcggatcggcgagcaggaggacgtccagcggaggtggca
ggacctgatccccgcgtgcagctggccgtcgagaccggggtcgacccggcgtcggcgga
ggggcgggcgctcgcggccgagtggatgggcctgctggaggatttccacggtggcgacac
cgggctgcgggactcgctctaccgcatgcaggcggacaacagcgagcggatccagccgtga
gcacggcgggccgtcgccggagcagctggagttcatccggcgcgccagcgcctcgtgacg
acgaagggccacccgccggaacggggtggccttcatgtcgaagtgatcaggacagctt
gtgcatccagccgtgcgggtcggggcgtgtgccctcctggatgccggtcagttcggcgcg
cagcttcat<u>cgtcacctcgccgggctcg</u>

SEQ ID NO. 13: Sequence 5'-3' of ZP_10050304.1: coding sequence
of vr3 gene is in hold, the primers used for the amplification
of the flanking regions vr3_U et vr3_D are underlined.

<u>ccgaagtgctcgtcggcgatc</u>cggtcgaacggggcagaccgtagggcaggtcgctcgcc
tgcgagaacgggttgtccggtgtcatccagcgcggcccttctgtcctgtcgaccctccga
tctccgcgtcggaggacgtcttcttattcctaccgcgcttcggcgccggcggcaccaccc
cggccagatccgcactgtggtcgttgacgcgcaccacgaacgggcgcacctcggtgtagc
ggaccacggagatcgacgccgggtcgaccacgatccgctggaacgcgtgaggtgctgcc
ccagcgcgtcggccaggatggacttgagcacgtcgccgtggctgcacagcagccagacgg
cgtggtcgccgtgctcggcggtgatccgcgcgtcgtgctcgcgcaccgcggcgaccgcgc
gggcctgcatgcctgccaggccctcgccgccggggaacaccgcggccgaggggtgggcct
gcacgacccgccacagcggttccttgaccaggtccttcagctcgcggccggtccactcgc
cgtagtccacttcggacaggcgcggttcgacggtgcgggtgaggccccgctcggcgacga
gcggggccaccgtgttcttgcagcgcagcatcggcgagcacacgacctcggccagcggca
cgccggccagccgctccacgagcgcctgagcctgcgcgcggccggtgtcgtcgagcccga
ccttgggggtccgcccggccagcacgcccgacccgttcgcggtcgagcggccgtgccgaa
gcaggatcacggtagccacgccgccaacctacatggcggggaccgcgttcggatcaagga
cgccggtggcgaccagcacgatgagcagcacgccgagcgcgatccggtagatcacgaacg
gcacgtagctcttggtcttgatgaagttcatcagccatgcgatcaccaggtagccgacgc
cgaaggcgaccagggtggccaggatcgtcggcccccactgcgggctgtgctcgccaccga
tgtcggtgagcttgtacaggccggaggcgaagaccgcgggcacggccagcaggaacgcgt
actcggtggcgtcggcgcgggtgtagccgaggaacaggcccgcggtgacggtgccgccgg
agcgggacacgccggggatcagcgccatggcctgggcgaagccgtagccgagaccatgcg
ggacggtgaggtggtccagcgtccggtactggcggcccaccggtcggcgatgagcagca
ggatgccgaacccgatcagcgtcgtcgcggtgaggcgcaggtcgcggaacgctgtcga
tggcgtcctggaacagcaggccgagcaccgcgatcggcagcgacccgacgatgatcagcc
agccgaggcgggcgtccgggtcgtggcgcgcctcccgctggtagagcgagcgccaccaag
cggccaggacgcggccgatcttcttcgagaagtagaggatgaccgccagctcggtgccga
tctgggtgaccgcggtgaacgccgccgccggggtcgtcccagccggcagcgccgcggtga
tgcgcaggtgggcgctggaggagatggggaggaactcggtcaggccctggaccaggccga
ggacgagtgcttcgaaccagcccatgctcaccgggccttcggggaaatcagtcgcgttcg
cacggtgggagaggctatcggcggcgcggatcactcgatgagccgccttcgtcaagttct
ttacagtactttcgttacgcccgcccgtcgcccaccgccaccctcaacggtggcgctccg
cgccgcagctacgccctcccgtctccaccgccaccctcaacggtggcgctccgcgccgcc
agctacgccctcccgtctccaccgccaccctcaacggtggcgctccg<u>cgccagctactctctg</u>
<u>tgc</u>atgcagaagcgacagctgggcaggtcggggttgcgggtctccggatggcgctcggc
acgatgtcctagggcgcggagaccgacgccgacgaggcggccagccagctcgtcgcgttc
gtcgaggcgggcgggacgctcgtggacaccgccgacatctactccggcggcgagagcgag
cggatcctcggggcctgctgggcgacctggtgccgcgtgacgagatcgtcgtggcgacc
aaggcgtcgcccgcgcaccgacgggccgttcggcaggggcgcctcccgcggcgcgttg
ttgtccgcgttggaggggtcgctcggcggctcggcgtgaccacctggacctgtggcag
ctgcacgcgtgggacgactcggtgccgctggaagagacgctgtcggcgctggaccacgcg
gtgacctcgggcaaggtccgctacaccggggtgtgcaactacgcgggctggcagctggcc

SEQUENCES 1-16

```
tcggccgcggcggcccggccggccgggctggtcgccacgcaggccgagtactcgctggtg
gagcgcggggtggagcgcgagctggtcccggcggcccgccaccacgggctcggcgtgctg
ccgtgggcgccgctgggccgcggggtgctgaccggcaagtaccgccacggcacgccggcc
gactcgcggggcgcgtcggccgagtacgccggctacgtcgagcagcaccgcaccgagcgg
gcggcgggatcgtcgaggcggtcgccaccgcggccgacgggctgggggtgtcgccgctg
gtggtggcgctggcgtgggtgcgggaccggccgggcgtggtcgcgccggtggtcggggcg
cgcgacaccgggcagctgacccgggtcgctggcggcggaggagatcgccctgccggtcgcg
atctcctcggcgctggacgacgtcagcgcggtcgagttcggttaccccgagcggggcacg
aagtgaccgtggggtggatggcacgtgacgcggcggggtttcagggggatgctggaggaa
acagaggaatgcgatccggaggtcttgtgcgctcctccgccaccgtcgggaccggtgtcg
tgctggtctgcgccctggtgctgagcgggtgctcgtcgaagtccggtgactccaccgaca
cgctgcaggtcgtggccgaccggtcgcggcgacggcgccgtgtcgccccagcctgccg
ccgccccgcgggcaccgtgatcgcctcccccgagatcaccgcgctggccgccgacccgg
ccaccgggacgctggccgtcgccgtgccggacgccgtgctgctgtaccaggccgctgacc
tggcggccgccccggtgcgggtgccggtcgccgggcgggccgagcacctgcgcgtgtccg
gcggggtgctgctggccacgctccccgcggccgggcaggtcgcccggatcgccttgcccg
gcggcgaggtgagcaccctggccgtggccggtcagccggccggcgcggtggtcgagggcg
accggacggtggtcgcggtgcgggaccgcaaggccgtggacgtgttcaccggcgaccagc
tgaccaagacgatcgagggccagctctacagcgccgacgacgtgctgcaggccggcggga
acaccgtcgtgctggacgagttgcgcaccgccgtgttctcggtggacgtggacggcggca
ccgtggccgagggcctgcgcgccggcgacggcgccaccaacgcggtcgcggactccttcg
gccgggtgctcgtggtcgacacccgcgccggtgccctcctggcgttctccaccggcccgc
tgttgctgcggcagcggtaccggttcccggcggggcgtacggcctcgcctacgacgcgc
agcgcgcgctggcgtgggtgacgctcaccgagcgcaacgaggtcgtcgggttcgacgtgc
gcggcggcgaaccggtcgagaagtaccgtttcccgacggtccggcagccggattcggtta
ccgtcgaggagcggagcgggcgggtggtcgtcggctccgcggcgggagaaggggtccagg
tgatccagccatgaagcaccaggaggcggtggtcgacgaggactgggagtaccgccggtt
gcagttgccaccccggcgtctcccggcggggccgcggccacgcagctgtccatcaacgccga
gtacggcgggtgggagctctcgacggtccggctctactccgacggcaccggcgggtgtg
gctgcgccgcaagcggcagccggccaccgccctgcccgaggtcctgatctgacccgagcg
gcgcccgcagctgggcgccgggcccagagccgcccctcgacggatgcgctacgcgcgaa
gagcggtaacggtggggccctcgtgtcgatctcagtgctgcccttggaaggagcagca
tgtcctcctcgccgtgtccgtgtcgtgaccgccgcctgcgccggggtcgcggtggcg
tggcgttgctggcggtcttcgccgggatgggcgtggcgctggtggtgctgatgggcatcg
tcgcgctggtcacatgcgtcccggtgtggttcgcgccggtgttgctcgcccgccgccgcg
gtgtggccgacgtccggccgatcgcggtgttcaccctcctggcggggtggtccctcatcg
gctgggtcgccgcgctgatctgggccggcgcggcgcgcggaagccggggccccgcccgg
tcgggacctagcccgcgagtgagcggcccgtctcctcgagcgcttcgcggaggatgcgca
cggctttggggcccatgccgtgcagggtgagcagctcggcctccgtcatggcggcgacct
ggtcgagcgtggtgatcccggcgttgcccagcgcgcgggtggcggggcggccgatggccc
gcggcaggtcgccgctctcgcccgccaccgccgcggtggccgtgcccgcga
```

SEQ ID NO. 14: Sequence 5'-3' of ZP_10054514.1: coding sequence
of vr4 gene is in bold, the primers used for the amplification
of the flanking regions vr4_U and vr4_D are underlined.

```
acgtcaaccggaacgggttgcaggaccagggcgagcccggcatcgccgacgtgggcgtgc
ggctgcagaaggccgacggcaccccggtcgcgggacgagcaccggcccgcacggccagt
accagttctcgcacctgcccgacggcagctaccaggtctgcttcgacaccgcgaagctcc
cgccgcagtacggcgactaccagctcaccaggcagcgcgcgggcgcgcgggccaggact
ccgcgcccgacccggccaccggctgcaccgcgccgaccgagctgaccccgagccgtaccc
aggacttcacgatgaacgccggcctggccgccgccggtcaaccggatcgccgcgctggtct
ggcaggacgtcgacggcgacggcgcgccgggagcgctggagccggggatcgccggggtgc
cggtgaagctgcgcggcgcggacggcacccaggtcgccatgaccaaccaccggccaggacg
ggaagtactccttcgacgacctgccgtccggctcgttcgcggtgtgcttcgacctggcca
acctgccgcaggccgcggccgacttcacgccggttgaggggagcccggtctccggcgccg
acccggcgaccggctgcaccccgcaggtgaccctcggcctcggcaagcgcgaggacaccg
cgctgaacatggggctcgccgcgcctgccaaccggatcggcgaccgggtgtgggcggaca
cgaaccgcaacggcatcgccgacgccaccgagtccggctcgacgggtgccggtcaagc
tgctccgcgccggcggcggcgaggaggcgtcgacgaccaccggcgccgacggccggttcc
ggttcaccgggatcccggacggtgcgtaccaggtgtgcgtcgaccgcgccgcgctgcccg
cgccggtggccgggtaccagttcacgaagccgcgcgccggtgagtccacaaaggattccg
atgtggacctggcgagcgggtgcgccccgccggtcgccgtcggcgtcggccaccgcgacg
agagcaccatcggcgtcggttgtcgcccgcgcgcaaccggctcggcgacctgctgtggg
tggaccgcaacggcaacggcacgcaggacgcgggagagcccggcgcggccggggtcccgg
tgacgctgaccgacgacggagggcgcccggtggcgaccaccgcaccgccgcggacggct
cgtacctgctcgacgacctgcccgacggctcgtaccgggtgtgcttcgacctcgccggcc
tcgccccggagttccgcggcttccacatcgcaggcggcgaccgggctgccgggaccgg
tgaccgtcggcccgaagccgcgggaggacctgtccgtgcggatcggcctcgtcagcgcca
gtccggcggtcgtgcctgccgcgcaggagtccacgagcggcggcgggttcccgtcgggt
gggtgttcggtgtcgtggcggcgatcggcgcggtcgtcggggtgcgctggtggaagg
ccgccgagcggagcgtgacccggtagtttgggcgttatgagaattctgcgggtgctcg
gagtcgtcgggatggcggtcgtgctgccggttgtgcgggaagccggggagacggcggacc
gggtgagcgcgtgctcgcaggccctcgggctggcgaacctcaacccgtacgcctcggcgc
aggaggtgtccgcccaggcgcagcagaaggccgaggagctgcgcaacctcggcaaccggg
tggccgaccagacgctgcagcagaacctgttcgcgatcgccgactcctacgtcgcgctgg
agcagcgcaagtcgcagggcctgtccgacgtgaacgactgggtccagacgaacaccgcca
acctggagcggctgcgccaggcctgcacgtgaggcggcggcaggccggctgtccccggga
```

SEQUENCES 1-16 ctcctaggatcgccggggctctgcctgttccgcggcgcgcggggatcgtggagcccgaa
caagccgagaagggatttcc
atgacagcgaacacactagccggcggcaccttcaccctcg
caggcgggctcaccgtcgggcgcatgggctacggcgcgatgcagctggccgggcctggcg
tgttcgggccgcccgcggaccgggacgccgcggtcgcggtcctgcgcgaagcggtcgagc
tgggtgtcaaccacatcgacaccgccgacttctacggcccgcacgtgacgaaccagatca
tccgcgaggcgctgcaccctacgacgggatcgtggtggtgaccaaggtcggcgcggtgc
gcgacgaccagggcgcctgggtgcaccagcgctcgccggagcagctgcgtgcccaggtgc
acgacaacctgcgcaacctcggcgtcgacgcgctcgacgtggtcaacctgcgcgtcggcg
gcggggacgacggccactccgcggtgcccggctcgatcgccgagccgttcaccgcgctgg
tcgagatgcagcaggaggggctgatcaagcacctcggcatcagcacggtcaacgccgagc
aggtcgccgaggcgcagtcgatcgcgccggtcgtgtgcgtgcagaacgcctacaacgtgg
cccaccgcgaggacgacaagctggtcgagtcgctggccgcgcagggcatcgcgtacgtgc
cgtacttcccgctcggcgggttctcgccgctgcagtcggaggtgctgaactcggtggccg
cccgcctcggcgcgaccccgatggccgtcgcgctggcctggctgctgcagcggtcgccga
acatcctgctcatcccgggcacgtcgtcggtcgcccacctgcgggagaacgtagccgccg
cgtccctggacctcccgcgggacgcgatcgccgaactcgacgcgatcgcctaa
cgcacca
cgaggtggagccccggccggccgtctcccggtcgacgaccgtggtctcgttccagccgc
ggggccgccctcgaacagcagggcgcggacccgcggcaggcggcgcaggtgacggcaga
aggacgccttgcgcagcacccggccgcgcgcgttgcccggccagcgcctccgccgggg
tgcagtccaccacacagcaggtgccgccgccgtccggtgagcagcccggtcagcatcagcc
acgccctggtcgccgcgccgatggccgggtcgtgcacaacgaccgggccgggcgtgcgga
tcgccgcgagcaccaccgcagccggtgcaggacgtgcaccgccgggcggtagcggcggt
acggcgtgccgggcggcagcgcggcggccagccggtcgcgcatctggtcggagtcgagca
cctcgaccgggcggctggcctgcgtgctgcgcagcagcgtgctcttgcccgaaccgggca
gcccggcgatgaccagcagcgcgcggttcgatcgtcatctgcaaggtggcgccggctg
tgctgtccataccgggccaacgcgcgatcacgccacccgcgttccgcacttacaggtcaa
atcggtcattcacagcggcgccacagcccgggaccctggccgagcggcggcgcagcccgaa
ggccaccgcgggcgaagccgagcccgaacaggcccgccgccgcgaagcccccagccggggcc
ggtgtggtcgatcacgaacccgaccaccgggctgcccgccgccatgccgagccgggtggc
ggcgtcgagcaggccatcgcctcgccgcgcaccgtggcggcgcgaggccggtgacctc
ctcggcggtcgacgcgagcgtcggcgcgcaggccaggttcgtcggcaccagcgccagcgc
cagcagccaccacggcagcccggtggccaacccgaccgggatcacgacacggtcagcag
caccatcagccgcgcctgcgacagcgacttccgcaccgcccgtgcacgatcccgccgac
cgccgaggcgacgcacatcacggcgatcaccacgccggtccagcccacctcgccggtggc
ccgcagcgcggcgagcgtcgccagttcggtgcccatcaggcagaacagcgccccgacgc
gacgagcagggcgccgaccagccgcgggctgagccactcccgcatcggcggccgctcggc
ggtgaccgtctcgccctcgtgccggatcggcgggttgaaccagcacagcgcgagggtgcc
gagcgcgaaacagacgccgatcccgctcagcgcgacggtcgaggacagctgcgtcgacag
ggcgatgcccgcgctcgggccgaccatgaagctcgtctccagcaggatcgagtcgagcga
gtacgccgagcgccgcgactccggcggcaccagcgcggtcagcacctggcgggcgatcga
gctggcaggcagcacgagcgcgcccgccggcacgcggtcacgacgacgccgcgcgtacgg
caggtgcggggtggccagccagaacgccgcggaggtcaggccgcacaccgaggtgaccgc
gcgcagcccgtagcggtcgatcatccggccgacgaccggcgccgatggcgctgcccag
catcgtcgcggtcccgacgagacccgcctggccgtacccgcggccgaggtcgctgacgac
gtgcagggtcagcgtgatcccggtggcggtcatcggcaggcgggtgaagaagaacagcag
catcgccatgcggaccccgggcagggcgaggacctggccggtacggctggagggacatgct
cccactttggcacggccgtgcaactccttttcgccgcttgccgctccggaaaactgac
agttactatcaaaaagtagtgactatcagtttggaggctgggatggacgggtcgaagcgg
tggtgggcgctgggtgcgctggccgtggcgttgctggcgttcggactcgat
gtgacggtc
ctgtcggtggcc SEQ ID NO. 15: Sequence 5'-3' of ZP_10050147.1: coding sequence of vr5 gene is in bold, the primers used for the amplification of the flanking regions vr5_13 and vr5_D are underlined.

gcggcagatcgagcagatccgcgacgcggtggaactcccgttcctgcacgccgacctcta
ccgggagtacgagctgcggccgcccaagggcgtcctgctctacgcccgccggttgcgg
caagacgctgatcgcaaggcggtggccaactcgctggccaagaaggtggccgaggcacg
cggggacggcgactcgaaggacgccaagtcctacttcctcaacatcaagggcccggagct
gctcaacaagttcgtcggcgagaccgagcggagcatccgcctgatcttccagcgggctcg
ggagaaggcctccgacggcacgcccgtgatcgtgttcttcgacgagatggagtcgatctt
ccgcacccgcggcagcggcgtctcctcggacgtggagaccacgatcgtgccgcagctgct
ggccgagatcgacggtgtcgaggggctggagaacgtcatcgtcatcggcgcctccaaccg
cgaggacatgatcgacccggcgatcctgcggccgggccggctggacgtgaagatcaagat
cgagcggccggacgccgagggtgcgaaggacatcttctccaagtacctgacgccggggct
gccgatccacgccgacgacctcgccgagttcggcggggacgcgcaggccacgatcgacgc
gatgatccagaacaccgtcgagcggatgtacgaggagacggacgagaaccggttcctcga
ggtcacctacgccaacggtgacaaggaggtcctgtacttccgcgacttcaactcggggcgc
gatgatccagaacatcgtgaccgggcgaagaaggccggcgatcaagtcggtgctggagac
caagcagcccggtctgcgggtgcagcacctgctcgacgcgatcgtcgacgagttcgcgga
gaacgaggacctgcccaacaccaccaacccggacgactgggcccggatctcgggcaagaa
gggcgagcggatcgtctacatccgcacgctggtcaccgggaagaaccaggagtccggccg
ggtcatcgacacggccacgaacaccggccagtacctgtaaccgcaggtgggccaggggag
gccgccgatccgtcggggtcggcggcctccgccgtgtcaggggcgcgccgcgcggccc
cgccagtaggcgagcagcaccccgccggccacgaccagcatgcaccgatcatcagggg
cacgttcggcccggcgcaggacagcgagtccggcgtgcagctgcggaacggcccgccctg
cccgctggagtcgtaccgctccgccgagaacaggaacaccagcaccgccatgccgtgcac
ggggcgaggaggaccgtcacggcgagcgcggccgcgccggcgcggagccgtcggatgat
cttgtcgggcacgtcgagaagacgcttcccggcgggttccggttgcccggcgtgtcgtccg

SEQUENCES 1-16 ccggtggccgtataacgacctatactgcgcgccatgaccgagcccgcggccgagatccgc
gccccgatcaccgaaaccgacgtcctggcctggctcgaggagaccgcgcaggcggtccgc
gcgcacgccgtcccgccggaggagctgatccggctgctggggagttgcggcgcgcgtcg
gcggcctgtgccgacgcgtcggactgggtgctgctggcggcgcgggaggaggggccagc
ctgcgccagatcgcgccggtcttcggcaagggctacgtgcgggcgccggcggcgcggctg
gagaagctccaccggcaggcgctgaactccgagcagtggctggagatcctccgtcaacga
gcatcaggcgtataacgacctatacgcggcggctttcggcgaaaaaccaccggtggcccg
ctccgcgggcgccccggaaaaaccgcacggaaaggacagtccccctgcgaatcggactcg
gcctggcggccctcgggcggccgcctatatcaacctcggccggagcagcgagctcccgg
tccggcgggacgtgcgacgatgcgcgaggcgacgttcgcggtgctcgacgcggcgtacg
cggccggtgtgcgctggatcgacgtcgcccgctcctacggccgggccgaggagttcctgg
ccgggtggctggccgagcgcggccacggcgacctcaccgtgccagcaagtggggctaca
cctacgtcggcggctggcgcatggacgccaccatacacgaggtgaaggagcactcggcgg
gcgtgttctcccgccagtggaccgaaagccgctcgctgctcggcaacgccatcaacctct
accaggtgcactcgctcaccgtggacagcccgttgttcaccgacgaggcgctgcagcggg
cgctggcggcgctcagcgacgacggcgtgcgcgtcgggttctccacttccgggccgaagc
aggcggaggtgatccgcgggagttcgagctggaagtggccgggcggccggcgttctcgg
ccgtgcagtcgacctggaacctgctcgaaccgtcggcaggccggcgctcgcggaggcgc
acgcggccgggaacctggtgctggtcaaggaaaccctcgccaacggcaggctggtggtca
acccgccgccgcgatcacccgcctggcgcaacgctacgcagtcggcgccgacgcggtgg
cgatcgcggcggtgctcgcccagccgtgggcggacacgtcctcatcggcccgtccagcc
cgcagcagctggccgccaacctcgccgcgaacggcgtcgacctgccacggggcgaactcg
cggcgctgcgggcgctggccgagccgccgaacggtactgggatcggcgatcctcgctgc
agtggcagtgaaggcttcgactaatctcagcgcccacaacgcatactgaagggaacgtca
ccgtgcgtcatggagggatggtggtcctggccgcggtcgtgctgaccgggctcaccgggt
gcgcggatcgcccgaacgacctggagacctactacgacaagccggcggacgcgacgacgc
cggtgacggcgccgtcggtctcgacgagcgtctcggtcggccaggcggcggcgaacaccc
cggtgaaccacatcgccgaggacgtggccgcggcggtgctcaccaagagcgacctgtccg
gcgagggcgtgcgggaggcggcggcccgcgccgccaacggatcctgcttcgacgccgtgc
ccgccggggacccgcgtggctcgacctggctctacaacagcggttcctcgctgacgcagc
aggtcaccggctacctcgaccgcaccgcggccgaggtgctcgcgcaggtcgactgcgacg
gcacggcgctgacggtcgccgcccggccggcgcggaggccgcgcgcgcctggtgcgacg
gcaccacctgcacgctgctgctggccggcggggcacgtgctgtccggcctgcaggtcaccg
cgagcacgcagaaccgggccgggaagcggtgaagggcctggcgtcgctggccgccggga
agctgccgcggagctgaccgccgacgggaaagcgctaccgcggcggaaccactcgtg
gatcgcgtgcctgccgtcgggcacgaaagggctttccgggtcctccgcgaaggcccgcag
ctcgtccaggggcatccaccggccggagacgattcctccggctggtggacgaccgggcc
gtcccagcgcgcctcgtaggcgaagtagtggcagcgcaccggcggctgctcgaacgtgaa
cgtgaacaggggtcgcaggggcacgccgcgcacgcccagttcctcggccagctcccgttc
cgcgccctcggcgggtgcttcgcccgccgcgaccacgccgcccgcccagcagtcgtacag
gccggggaagacgtccttgtccggtgagcgccggtgcacgtacacgcgggagccgtcccc
ggagcgcaccagcaccagcgtcgcggcgtgccagagcccctgttcgcggcatgtcggcgcg
gcgcaccggctcacgaccacgcccgcggcgtcgtagtgggcgaccatttcatcagcact
gctcaccatcttgcgccagcatgacagatccgggtgctttacctggtcgcaaccggtggc
ccactcaccgttgccgcccgcgacccgtaggcttgggacatgcgggatcatgggaacc
gaagtcgagtacggcatcgccgtgccgggcgacgcgacggccaacccggtactgacatcg
acgcaggtcgtgctggcctacgcggcggcggcggacatcccgcgggcgcgccgcgcgcgg
tgggactacgaggtggagtcgccgctgcgcgacgcccgtggtttcgacctggccgggccg
ggcggcggggcacgaccggaacgtggaggacctcggcgcgcaacgtcatcctgacc
aacggcgcccggctctacgtcgaccacgcgcacccggagtactcggcgcccgaggtgacc
aacccgcgggacggggtcatctgggacaaggcgggcgagcgggtgatggaggaggccgcg
atgcgggcggccaccgtgcccgggcagccggtgctgcagatgtacaagaacaacgtggac
ggcaagggcgccagctacggcacccacgagaactacctgatggcccgttcgacgccgttc
acctcggtgatcgccgggctgacgccgttcttcgtgtcccggcaggtggtgaccggttcc
ggccgggtgggtatcggcccgcagggtgaggaggccggcttccagctgtcgcagcgctcg
gactacatcgaggtcgaggtcggcctggagacgacgctgaagcggggatcatcaacacc
cgcgacgagccgcacgcggac SEQ ID NO. 16: Sequence BglII_ermE_RBS_vr1_XbaI. The 5'-3' coding sequence of vr1 gene is in bold, the promoter ermE is underlined, and ribosome binding sequence (RBS) are in capital characters. The added BglII forward primer and XbaI reverse primer are in italics.

*gagatct*gttgtgggctggacaatcgtgccggttggtaggatccagcgggtaccaatacg
AAGGAGGCAACAAGatgagataccggcttttcgggcgcaccgggctgcgcgtggcggaga
tgttcctcggggcgatggcgctgcaggaaccggacgaggcgcggcgggtggtcaaggcct
acgccgacgccggggcaacgtgatcgacacggcctcggcgtacgcggagagcgagaacg
tgctgggcgaggtgctgaccgaccgcgaccggttcgtgctggccaccaagtacacgctga
cgcgggatccgcacgacccgaacgccggggcagccaccgcaagaacctggtcgcgtccc
tggagcgcagcctgcggcggctgcgcaccgactacgtcgacatcctgtgggtgcacacgt
gggaccgcacacgccggtcgccgagacgctgcgtgcgctggacgacctggtgcgggccg
ggaaggtcaggtacctcggggtgtccgacacgcccgcgtgggtggtgagccgggccgacg
tgctggcggagtggcgcgggtggacgccgttcgccggggtgcaggtgccctacagcctgc
tgaaccgcgacatcgagcgcgacgtgctgccgatggccgagcagctgggcctgaccgtcg
cggcgtggggcgtcctggagcacgcgcgctgaccggtccagccgggtcggttcgccgt
cgccggagcagcagcgggtggcggcggcggtgcgcgcggtggcggacgagctgggtgtca
cgccggcacaggtggcgatcgcgtggtcgcggggcgcggtcggcggtcgtgcacccgctga

| SEQUENCES 1-16 |
|---|
| tcgggttccggacggcggaccgggtcgcggagagcgtcgccgccctggacgtgacgctgc
ccccggaagcggtggcgaagctggaggcggcggcgccgttcgagccgggccgttcgcg
acttcgtgaaccagtcggcggccagcgccggggtgttcggccacggcgaggtggtggcgc
gtcagctgcgggagtgatctagacctcc |

The invention claimed is:

1. A recombinant strain belonging to the order of Actinomycetales, wherein at least one gene encoding an enzyme having vanillin reductase activity is non-functional, wherein
said gene encoding an enzyme having vanillin reductase activity comprises a sequence having at least 90% of nucleic acid identity with a sequence selected in a group comprising the sequences SEQ ID NO: 1, SEQ ID NO: 3, SEQ ID NO: 5, SEQ ID NO: 7, and SEQ ID NO: 9; and/or
said enzyme having vanillin reductase activity has an amino acid sequence comprising at least 90% of amino acid identity with a sequence selected in a group comprising the sequences: SEQ ID NO: 2, SEQ ID NO: 4, SEQ ID NO: 6, SEQ ID NO: 8, and SEQ ID NO: 10; and/or
at least one gene chosen among the genes comprising the sequences as shown in SEQ ID NO: 1 (vr1), SEQ ID NO: 3 (vr2), SEQ ID NO: 5 (vr3), SEQ ID NO: 7 (vr4) and SEQ ID NO: 9 (vr5) is non-functional.

2. The recombinant strain of claim 1, wherein said strain is from the genus *Amycolatopsis* or *Streptomyces*.

3. The recombinant strain of claim 2, wherein said strain is the strain *Amycolatopsis* sp. accessible under number ATCC 39116.

4. The recombinant strain of claim 1, wherein at least one endogenous gene encoding an enzyme having vanillin reductase activity has been deleted.

5. The recombinant strain of claim 1, wherein at least one endogenous gene encoding an enzyme having vanillin reductase activity has been replaced, totally or partially, with a DNA cassette.

6. The recombinant strain of claim 1, wherein at least one endogenous gene encoding an enzyme having vanillin reductase activity has been inactivated by introduction of a DNA cassette.

7. The recombinant strain of claim 5, wherein the DNA cassette has been removed from the genome to obtain a marker-less recombinant strain.

8. The recombinant strain of claim 5, wherein the DNA cassette comprises two sequences (1) and (2), each one having a length of about 2 kb.

9. The recombinant strain of claim 1, wherein said gene encoding an enzyme having vanillin reductase activity comprises a sequence having at least 95% of nucleic acid identity with a sequence selected in a group comprising the sequences SEQ ID NO: 1, SEQ ID NO: 3, SEQ ID NO: 5, SEQ ID NO: 7, and SEQ ID NO: 9.

10. The recombinant strain of claim 1, wherein said enzyme having vanillin reductase activity has an amino acid sequence comprising at least 95% of amino acid identity with a sequence selected in a group comprising the sequences: SEQ ID NO: 2, SEQ ID NO: 4, SEQ ID NO: 6, SEQ ID NO: 8, and SEQ ID NO: 10.

11. The recombinant strain of claim 1, wherein at least one gene chosen among the genes comprising the sequences as shown in SEQ ID NO: 1 (vr1), SEQ ID NO: 3 (vr2), SEQ ID NO: 5 (vr3), SEQ ID NO: 7 (vr4) and SEQ ID NO: 9 (vr5) is non-functional.

12. The recombinant strain of claim 1, wherein at least two genes encoding an enzyme having vanillin reductase activity are non-functional among the genes presenting the sequences as shown in SEQ ID NO: 1 (vr1), SEQ ID NO: 3 (vr2), SEQ ID NO: 5 (vr3), SEQ ID NO: 7 (vr4) and SEQ ID NO: 9 (vr5).

13. The recombinant strain of claim 1, wherein the five genes comprising the sequences as shown in SEQ ID NO: 1 (vr1), SEQ ID NO: 3 (vr2), SEQ ID NO: 5 (vr3), SEQ ID NO: 7 (vr4) and SEQ ID NO: 9 (vr5) are non-functional.

14. The recombinant strain of claim 1, wherein at least one gene encoding an enzyme having vanillin dehydrogenase activity is non-functional among the genes presenting the sequences as shown in SEQ ID NO: 1 (vr1), SEQ ID NO: 3 (vr2), SEQ ID NO: 5 (vr3), SEQ ID NO: 7 (vr4) and SEQ ID NO: 9 (vr5).

15. A process for producing vanillin, comprising culturing the recombinant strain of claim 1 in an appropriate medium comprising a substrate, and recovering the produced vanillin.

16. The recombinant strain of claim 6, wherein the DNA cassette has been removed from the genome to obtain a marker-less recombinant strain.

17. The recombinant strain of claim 6, wherein the DNA cassette comprises two sequences (1) and (2), each one having a length of about 2 kb.

18. A process for producing vanillin, comprising culturing the recombinant strain of claim 4 in an appropriate medium comprising a substrate, and recovering the produced vanillin.

19. A process for producing vanillin, comprising culturing the recombinant strain of claim 5 in an appropriate medium comprising a substrate, and recovering the produced vanillin.

20. A process for producing vanillin, comprising culturing the recombinant strain of claim 6 in an appropriate medium comprising a substrate, and recovering the produced vanillin.

21. A process for producing vanillin, comprising culturing the recombinant strain of claim 11 in an appropriate medium comprising a substrate, and recovering the produced vanillin.

22. A process for producing vanillin, comprising culturing the recombinant strain of claim 13 in an appropriate medium comprising a substrate, and recovering the produced vanillin.

* * * * *

SEQUENCE LISTING

<160> NUMBER OF SEQ ID NOS: 36

<210> SEQ ID NO 1
<211> LENGTH: 963
<212> TYPE: DNA
<213> ORGANISM: Amycolatopsis sp.

<400> SEQUENCE: 1

| | | | | | |
|---|---|---|---|---|---|
| atgagatacc | ggcttttcgg | gcgcaccggg | ctgcgcgtgg | cggagatgtt | cctcggggcg | 60 |
| atggcgctgc | aggaaccgga | cgaggcgcgg | cgggtggtca | aggcctacgc | cgacgccggg | 120 |
| ggcaacgtga | tcgacacggc | ctcggcgtac | gcggagagcg | agaacgtgct | gggcgaggtg | 180 |
| ctgaccgacc | gcgaccggtt | cgtgctggcc | accaagtaca | cgctgacgcg | ggatccgcac | 240 |
| gacccgaacg | ccgggggcag | ccaccgcaag | aacctggtcg | cgtccctgga | gcgcagcctg | 300 |
| cggcggctgc | gcaccgacta | cgtcgacatc | ctgtgggtgc | acacgtggga | cccgcacacg | 360 |
| ccggtcgccg | agacgctgcg | tgcgctggac | gacctggtgc | gggccgggaa | ggtcaggtac | 420 |
| ctcggggtgt | ccgacacgcc | cgcgtgggtg | gtgagccggg | ccgacgtgct | ggcggagtgg | 480 |
| cgcgggtgga | cgccgttcgc | cggggtgcag | gtgccctaca | gctgctgaa | ccgcgacatc | 540 |
| gagcgcgacg | tgctgccgat | ggccgagcag | ctggggctga | ccgtcgcggc | gtgggcgtc | 600 |
| ctggagcacg | gcgcgctgac | cgggtccagc | cgggtcggtt | cgccgtcgcc | ggagcagcag | 660 |
| cgggtggcgg | cggcggtgcg | cgcggtggcg | gacgagctgg | gtgtcacgcc | ggcacaggtg | 720 |
| gcgatcgcgt | ggtcgcgggc | gcggtcggcg | gtcgtgcacc | cgctgatcgg | gttccggacg | 780 |
| gcggaccggg | tcgcggagag | cgtcgccgcc | ctggacgtga | cgctgccccc | ggaagcggtg | 840 |
| gcgaagctgg | aggcggcggc | gccgttcgag | ccgggcccgt | cgccgacttc | cgtgaaccag | 900 |
| tcggcggcca | gcgccggggt | gttcggccac | ggcgaggtgg | tggcgcgtca | gctgcgggag | 960 |
| tga | | | | | | 963 |

<210> SEQ ID NO 2
<211> LENGTH: 320
<212> TYPE: PRT
<213> ORGANISM: Amycolatopsis sp.

<400> SEQUENCE: 2

Met Arg Tyr Arg Leu Phe Gly Arg Thr Gly Leu Arg Val Ala Glu Met
1               5                   10                  15

Phe Leu Gly Ala Met Ala Leu Gln Glu Pro Asp Glu Ala Arg Arg Val
            20                  25                  30

Val Lys Ala Tyr Ala Asp Ala Gly Gly Asn Val Ile Asp Thr Ala Ser
        35                  40                  45

Ala Tyr Ala Glu Ser Glu Asn Val Leu Gly Glu Val Leu Thr Asp Arg
    50                  55                  60

Asp Arg Phe Val Leu Ala Thr Lys Tyr Thr Leu Thr Arg Asp Pro His
65                  70                  75                  80

Asp Pro Asn Ala Gly Gly Ser His Arg Lys Asn Leu Val Ala Ser Leu
                85                  90                  95

Glu Arg Ser Leu Arg Arg Leu Thr Asp Tyr Val Asp Ile Leu Trp
        100                 105                 110

Val His Thr Trp Asp Pro His Thr Pro Val Ala Glu Thr Leu Arg Ala
        115                 120                 125

Leu Asp Asp Leu Val Arg Ala Gly Lys Val Arg Tyr Leu Gly Val Ser
        130                 135                 140

Asp Thr Pro Ala Trp Val Ser Arg Ala Asp Val Leu Ala Glu Trp
145                 150                 155                 160

Arg Gly Trp Thr Pro Phe Ala Gly Val Gln Val Pro Tyr Ser Leu Leu
                165                 170                 175

Asn Arg Asp Ile Glu Arg Asp Val Leu Pro Met Ala Glu Gln Leu Gly
            180                 185                 190

Leu Thr Val Ala Ala Trp Gly Val Leu Glu His Gly Ala Leu Thr Gly
        195                 200                 205

Ser Ser Arg Val Gly Ser Pro Ser Pro Glu Gln Gln Arg Val Ala Ala
    210                 215                 220

Ala Val Arg Ala Val Ala Asp Glu Leu Gly Val Thr Pro Ala Gln Val
225                 230                 235                 240

Ala Ile Ala Trp Ser Arg Ala Arg Ser Ala Val Val His Pro Leu Ile
                245                 250                 255

Gly Phe Arg Thr Ala Asp Arg Val Ala Glu Ser Val Ala Ala Leu Asp
            260                 265                 270

Val Thr Leu Pro Pro Glu Ala Val Ala Lys Leu Glu Ala Ala Pro
        275                 280                 285

Phe Glu Pro Gly Pro Phe Ala Asp Phe Val Asn Gln Ser Ala Ala Ser
    290                 295                 300

Ala Gly Val Phe Gly His Gly Glu Val Val Ala Arg Gln Leu Arg Glu
305                 310                 315                 320

<210> SEQ ID NO 3
<211> LENGTH: 990
<212> TYPE: DNA
<213> ORGANISM: Amycolatopsis sp.

<400> SEQUENCE: 3
atggagtttc gccgtctcgg ccgcagtggc ctgtccgtca gtgagatcgc ctacgggaac     60
tggctcaccc acggttccca gatcgacgag gaccaggccc aggcctgcat caaggccgcg    120
ctcgacgcgg gcatcacgac cttcgacacc gccgacgtct acgccaacac cctggcggag    180
tcggtgctcg ccgcggtct  ggccggtcag cgccgggaga gcctggagat ctgcacgaag    240
gtgttctggc cgaccggccc cggcggcccg aacgaccgcg ggctgggccg caagcacatc    300
atcgagtcct gccacgcctc gctgaagcgg ctgcagaccg accacatcga cctctaccag    360
gcgcaccggt cgaccccgac cgtgccgctg aggagacca  tgtcggcctt cgccgacctg    420
gtccgccagg gcaaggtgct ctacatcggg gtgtcggagt ggaacgccga ggagatcacc    480
cgcggcgccg cgctggcccg cgagctgcgg atccccttcg tgtcgaacca gccgcagtac    540
aacatgctct ggcgcgtcat cgaggcgcag gtcgtgcccg ccagcgagcg cgaggggctg    600
agccagatcg tctggtcgcc gatcgcgcag ggggtgctga ccggcaagta caagccgggt    660
cagccgccgc cgccgggtc  gcgcgccacg gacgagcggg gctcgcagtt cgtgcagcgg    720
ttcctgcggg acgaggtgct cgagcgcgtg gcccggctgg agccgctggc cgcgcaggcg    780

```
gggctgacgc tggcgcagct ggcggtggcg tgggtgctgc agaacccgaa cgtcgcctcc   840
gcgatcgtcg gcgcgtcgcg gccggagcag gtgcacgaga acgtgaaggc ggcgggcgtg   900
aagctcgacg ccgacctgct gaccgagatc gactcggtgc tgctgggcgt ggtcgaggac   960
gatccgcgcc tgaccgctcg cgccggctga                                    990
```

```
<210> SEQ ID NO 4
<211> LENGTH: 329
<212> TYPE: PRT
<213> ORGANISM: Amycolatopsis sp.

<400> SEQUENCE: 4

Met Glu Phe Arg Arg Leu Gly Arg Ser Gly Leu Ser Val Ser Glu Ile
1               5                   10                  15

Ala Tyr Gly Asn Trp Leu Thr His Gly Ser Gln Ile Asp Glu Asp Gln
            20                  25                  30

Ala Gln Ala Cys Ile Lys Ala Ala Leu Asp Ala Gly Ile Thr Thr Phe
        35                  40                  45

Asp Thr Ala Asp Val Tyr Ala Asn Thr Leu Ala Glu Ser Val Leu Gly
    50                  55                  60

Arg Gly Leu Ala Gly Gln Arg Arg Glu Ser Leu Glu Ile Cys Thr Lys
65                  70                  75                  80

Val Phe Trp Pro Thr Gly Pro Gly Pro Asn Asp Arg Gly Leu Gly
                85                  90                  95

Arg Lys His Ile Ile Glu Ser Cys His Ala Ser Leu Lys Arg Leu Gln
                100                 105                 110

Thr Asp His Ile Asp Leu Tyr Gln Ala His Arg Phe Asp Pro Thr Val
            115                 120                 125

Pro Leu Glu Glu Thr Met Ser Ala Phe Ala Asp Leu Val Arg Gln Gly
    130                 135                 140

Lys Val Leu Tyr Ile Gly Val Ser Glu Trp Asn Ala Glu Glu Ile Thr
145                 150                 155                 160

Arg Gly Ala Ala Leu Ala Arg Glu Leu Arg Ile Pro Phe Val Ser Asn
                165                 170                 175

Gln Pro Gln Tyr Asn Met Leu Trp Arg Val Ile Glu Ala Gln Val Val
            180                 185                 190

Pro Ala Ser Glu Arg Glu Gly Leu Ser Gln Ile Val Trp Ser Pro Ile
        195                 200                 205

Ala Gln Gly Val Leu Thr Gly Lys Tyr Lys Pro Gly Gln Pro Pro
    210                 215                 220

Ala Gly Ser Arg Ala Thr Asp Glu Arg Gly Ser Gln Phe Val Gln Arg
225                 230                 235                 240

Phe Leu Arg Asp Glu Val Leu Glu Arg Val Ala Arg Leu Glu Pro Leu
                245                 250                 255

Ala Ala Gln Ala Gly Leu Thr Leu Ala Gln Leu Ala Val Ala Trp Val
            260                 265                 270

Leu Gln Asn Pro Asn Val Ala Ser Ala Ile Val Gly Ala Ser Arg Pro
        275                 280                 285

Glu Gln Val His Glu Asn Val Lys Ala Ala Gly Val Lys Leu Asp Ala
    290                 295                 300

Asp Leu Leu Thr Glu Ile Asp Ser Val Leu Leu Gly Val Val Glu Asp
305                 310                 315                 320

Asp Pro Arg Leu Thr Ala Arg Ala Gly
                325
```

<210> SEQ ID NO 5
<211> LENGTH: 963
<212> TYPE: DNA
<213> ORGANISM: Amycolatopsis sp.

<400> SEQUENCE: 5

```
atgcagaagc gacagctggg caggtcgggg ttgcgggtct cccggatggc gctcggcacg      60
atgtcctggg gcgcggagac cgacgccgac gaggcggcca gccagctcgt cgcgttcgtc     120
gaggcgggcg ggacgctcgt ggacaccgcc gacatctact ccggcggcga gagcgagcgg     180
atcctcgggg gcctgctggg cgacctggtg ccgcgtgacg agatcgtcgt ggcgaccaag     240
gccgtcgccc ggcgcaccga cgggccgttc ggcggggggcg cctcccgcgg cgcgttgttg     300
tccgcgttgg agggggtcgct gcggcggctc ggcgtggacc acctggacct gtggcagctg     360
cacgcgtggg acgactcggt gccgctggaa gagacgctgt cggcgctgga ccacgcggtg     420
acctcgggca aggtccgcta caccggggtg tgcaactacg cgggctggca gctggcctcg     480
gccgcggcgc cccggccggc cgggctggtc gccacgcagg ccgagtactc gctggtggag     540
cgcggggtgg agcgcgagct ggtcccggcg gcccgccacc acgggctcgg cgtgctgccg     600
tgggcgccgc tgggccgcgg ggtgctgacc ggcaagtacc gccacggcac gccggccgac     660
tcgcggggcg cgtcggccga gtacgccggc tacgtcgagc agcaccgcac cgagcgggcg     720
gcgcggatcg tcgaggcggt cgccaccgcg ccgacgggc tggggggtgtc gccgctggtg     780
gtggcgctgg cgtgggtgcg ggaccggccg ggcgtggtcg cgccggtggt cggggcgcgc     840
gacaccgggc agctgaccgg gtcgctggcg gcggaggaga tcgccctgcc ggtcgcgatc     900
tcctcggcgc tggacgacgt cagcgcggtc gagttcggtt accccgagcg gggcacgaag     960
tga                                                                   963
```

<210> SEQ ID NO 6
<211> LENGTH: 320
<212> TYPE: PRT
<213> ORGANISM: Amycolatopsis sp.

<400> SEQUENCE: 6

Met Gln Lys Arg Gln Leu Gly Arg Ser Gly Leu Arg Val Ser Arg Met
1               5                   10                  15

Ala Leu Gly Thr Met Ser Trp Gly Ala Glu Thr Asp Ala Asp Glu Ala
            20                  25                  30

Ala Ser Gln Leu Val Ala Phe Val Glu Ala Gly Gly Thr Leu Val Asp
        35                  40                  45

Thr Ala Asp Ile Tyr Ser Gly Gly Glu Ser Glu Arg Ile Leu Gly Gly
    50                  55                  60

Leu Leu Gly Asp Leu Val Pro Arg Asp Glu Ile Val Val Ala Thr Lys
65                  70                  75                  80

Ala Val Ala Arg Arg Thr Asp Gly Pro Phe Gly Gly Gly Ala Ser Arg
                85                  90                  95

Gly Ala Leu Leu Ser Ala Leu Glu Gly Ser Leu Arg Arg Leu Gly Val
            100                 105                 110

Asp His Leu Asp Leu Trp Gln Leu His Ala Trp Asp Asp Ser Val Pro
        115                 120                 125

Leu Glu Glu Thr Leu Ser Ala Leu Asp His Ala Val Thr Ser Gly Lys
    130                 135                 140

Val Arg Tyr Thr Gly Val Cys Asn Tyr Ala Gly Trp Gln Leu Ala Ser
145                 150                 155                 160

```
Ala Ala Ala Ala Arg Pro Ala Gly Leu Val Ala Thr Gln Ala Glu Tyr
            165                 170                 175

Ser Leu Val Glu Arg Gly Val Glu Arg Glu Leu Val Pro Ala Ala Arg
        180                 185                 190

His His Gly Leu Gly Val Leu Pro Trp Ala Pro Leu Gly Arg Gly Val
        195                 200                 205

Leu Thr Gly Lys Tyr Arg His Gly Thr Pro Ala Asp Ser Arg Gly Ala
        210                 215                 220

Ser Ala Glu Tyr Ala Gly Tyr Val Glu Gln His Arg Thr Glu Arg Ala
225                 230                 235                 240

Ala Arg Ile Val Glu Ala Val Ala Thr Ala Ala Asp Gly Leu Gly Val
                245                 250                 255

Ser Pro Leu Val Val Ala Leu Ala Trp Val Arg Asp Arg Pro Gly Val
                260                 265                 270

Val Ala Pro Val Val Gly Ala Arg Asp Thr Gly Gln Leu Thr Gly Ser
            275                 280                 285

Leu Ala Ala Glu Glu Ile Ala Leu Pro Val Ala Ile Ser Ser Ala Leu
        290                 295                 300

Asp Asp Val Ser Ala Val Glu Phe Gly Tyr Pro Glu Arg Gly Thr Lys
305                 310                 315                 320

<210> SEQ ID NO 7
<211> LENGTH: 873
<212> TYPE: DNA
<213> ORGANISM: Amycolatopsis sp.

<400> SEQUENCE: 7
atgacagcga acacactggc cggcggcacc ttcaccctcg caggcgggct caccgtcggg    60
cgcatgggct acggcgcgat gcagctggcc gggcctggcg tgttcgggcc gcccgcggac   120
cgggacgccg cggtcgcggt cctgcgcgaa gcggtcgagc tgggtgtcaa ccacatcgac   180
accgccgact tctacggccc gcacgtgacg aaccagatca tccgcgaggc gctgcacccc   240
tacgacggga tcgtggtggt gaccaaggtc ggcgcggtgc gcgacgacca gggcgcctgg   300
gtgcaccagc gctcgccgga gcagctgcgt gcccaggtgc acgacaacct cgcaaacctc   360
ggcgtcgacg cgctcgacgt ggtcaacctg cgcgtcggcg cggggacga cggccactcc   420 gcggtgcccg ctcgatcgc cgagccgttc accgcgctgg tcgagatgca gcaggagggg   480
ctgatcaagc acctcggcat cagcacggtc aacgccgagc aggtcgccga ggcgcagtcg   540
atcgcgccgt cgtgtgcgt gcagaacgcc tacaacgtgg cccaccgcga ggacgacaag   600
ctggtcgagt cgctggccgc gcagggcatc gcgtacgtgc cgtacttccc gctcggcggg   660
ttctcgccgc tgcagtcgga ggtgctgaac tcggtggccg cccgcctcgg cgcgaccccg   720
atggccgtcg cgctggcctg gctgctgcag cggtcgccga acatcctgct catcccgggc   780
acgtcgtcgg tcgcccacct gcgggagaac gtggccgccg cgtccctgga cctccccgcg   840
gacgcgatcg ccgaactcga cgcgatcgcc taa                                873

<210> SEQ ID NO 8
<211> LENGTH: 290
<212> TYPE: PRT
<213> ORGANISM: Amycolatopsis sp.

<400> SEQUENCE: 8

Met Thr Ala Asn Thr Leu Ala Gly Gly Thr Phe Thr Leu Ala Gly Gly
1               5                   10                  15
```

Leu Thr Val Gly Arg Met Gly Tyr Gly Ala Met Gln Leu Ala Gly Pro
         20                  25                  30

Gly Val Phe Gly Pro Pro Ala Asp Arg Asp Ala Ala Val Ala Val Leu
             35                  40                  45

Arg Glu Ala Val Glu Leu Gly Val Asn His Ile Asp Thr Ala Asp Phe
 50                  55                  60

Tyr Gly Pro His Val Thr Asn Gln Ile Ile Arg Glu Ala Leu His Pro
 65                  70                  75                  80

Tyr Asp Gly Ile Val Val Thr Lys Val Gly Ala Val Arg Asp Asp
                 85                  90                  95

Gln Gly Ala Trp Val His Gln Arg Ser Pro Glu Gln Leu Arg Ala Gln
             100                 105                 110

Val His Asp Asn Leu Arg Asn Leu Gly Val Asp Ala Leu Asp Val Val
         115                 120                 125

Asn Leu Arg Val Gly Gly Gly Asp Asp Gly His Ser Ala Val Pro Gly
130                 135                 140

Ser Ile Ala Glu Pro Phe Thr Ala Leu Val Glu Met Gln Gln Glu Gly
145                 150                 155                 160

Leu Ile Lys His Leu Gly Ile Ser Thr Val Asn Ala Glu Gln Val Ala
                 165                 170                 175

Glu Ala Gln Ser Ile Ala Pro Val Val Cys Val Gln Asn Ala Tyr Asn
             180                 185                 190

Val Ala His Arg Glu Asp Asp Lys Leu Val Glu Ser Leu Ala Ala Gln
         195                 200                 205

Gly Ile Ala Tyr Val Pro Tyr Phe Pro Leu Gly Gly Phe Ser Pro Leu
210                 215                 220

Gln Ser Glu Val Leu Asn Ser Val Ala Ala Arg Leu Gly Ala Thr Pro
225                 230                 235                 240

Met Ala Val Ala Leu Ala Trp Leu Leu Gln Arg Ser Pro Asn Ile Leu
                 245                 250                 255

Leu Ile Pro Gly Thr Ser Ser Val Ala His Leu Arg Glu Asn Val Ala
             260                 265                 270

Ala Ala Ser Leu Asp Leu Pro Ala Asp Ala Ile Ala Glu Leu Asp Ala
         275                 280                 285

Ile Ala
 290

<210> SEQ ID NO 9
<211> LENGTH: 831
<212> TYPE: DNA
<213> ORGANISM: Amycolatopsis sp.

<400> SEQUENCE: 9
atgcgcgagg cgacgttcgc ggtgctcgac gcggcgtacg cggccggtgt gcgctggatc      60
gacgtcgccc gctcctacgg ccgggccgag gagttcctgg ccgggtggct ggccgagcgc     120
ggccacggcg acctcaccgt gtccagcaag tggggctaca cctacgtcgg cggctggcgc     180
atggacgcca ccatgcacga ggtgaaggag cactcggcgg cgtgttctc ccgccagtgg      240 accgaaagcc gctcgctgct cggcaacgcc atcaacctct accaggtgca ctcgctcacc     300
gtggacagcc cgttgttcac cgacgaggcg ctgcagcggg cgctggcggc gctcagcgac     360
gacggcgtgc cgtcgggtt ctccacttcc gggccgaagc aggcggaggt gatccggcgg      420
gcgttcgagc tggaagtggc cgggcggccg gtgttctcgg ccgtgcagtc gacctggaac     480

```
ctgctcgaac cgtcggcagg cccggcgctc gcggaggcgc acgcggccgg gaacctggtg    540
ctggtcaagg aaaccctcgc caacggcagg ctggtggtca acccgccgcc cgcgatcacc    600
cgcctggcgc aacgctacgc agtcggcgcc gacgcggtgg cgatcgcggc ggtgctcgcc    660
cagccgtggg cggacacggt cctcatcggc ccgtccagcc cgcagcagct ggccgccaac    720
ctcgccgcga acggcgtcga cctgccacgg ggcgaactcg cggcgctgcg ggcgctggcc    780
gagccgccgg aacggtactg ggatcggcga tcctcgctgc agtggcagtg a             831
```

```
<210> SEQ ID NO 10
<211> LENGTH: 276
<212> TYPE: PRT
<213> ORGANISM: Amycolatopsis sp.

<400> SEQUENCE: 10

Met Arg Glu Ala Thr Phe Ala Val Leu Asp Ala Ala Tyr Ala Ala Gly
1               5                   10                  15

Val Arg Trp Ile Asp Val Ala Arg Ser Tyr Gly Arg Ala Glu Glu Phe
            20                  25                  30

Leu Ala Gly Trp Leu Ala Glu Arg Gly His Gly Asp Leu Thr Val Ser
        35                  40                  45

Ser Lys Trp Gly Tyr Thr Tyr Val Gly Gly Trp Arg Met Asp Ala Thr
    50                  55                  60

Met His Glu Val Lys Glu His Ser Ala Gly Val Phe Ser Arg Gln Trp
65                  70                  75                  80

Thr Glu Ser Arg Ser Leu Leu Gly Asn Ala Ile Asn Leu Tyr Gln Val
                85                  90                  95

His Ser Leu Thr Val Asp Ser Pro Leu Phe Thr Asp Glu Ala Leu Gln
            100                 105                 110

Arg Ala Leu Ala Ala Leu Ser Asp Asp Gly Val Arg Val Gly Phe Ser
        115                 120                 125

Thr Ser Gly Pro Lys Gln Ala Glu Val Ile Arg Arg Ala Phe Glu Leu
    130                 135                 140

Glu Val Ala Gly Arg Pro Val Phe Ser Ala Val Gln Ser Thr Trp Asn
145                 150                 155                 160

Leu Leu Glu Pro Ser Ala Gly Pro Ala Leu Ala Glu Ala His Ala Ala
                165                 170                 175

Gly Asn Leu Val Leu Val Lys Thr Leu Ala Asn Gly Arg Leu Val
            180                 185                 190

Val Asn Pro Pro Ala Ile Thr Arg Leu Ala Gln Arg Tyr Ala Val
        195                 200                 205

Gly Ala Asp Ala Val Ala Ile Ala Ala Val Leu Ala Gln Pro Trp Ala
    210                 215                 220

Asp Thr Val Leu Ile Gly Pro Ser Ser Pro Gln Gln Leu Ala Ala Asn
225                 230                 235                 240

Leu Ala Ala Asn Gly Val Asp Leu Pro Arg Gly Glu Leu Ala Ala Leu
                245                 250                 255

Arg Ala Leu Ala Glu Pro Pro Glu Arg Tyr Trp Asp Arg Arg Ser Ser
            260                 265                 270

Leu Gln Trp Gln
        275

<210> SEQ ID NO 11
<211> LENGTH: 5175
<212> TYPE: DNA
<213> ORGANISM: Amycolatopsis sp.
```

<400> SEQUENCE: 11

```
cgcgcagctc cggcgatccg ttgcggtagg ccaggatgat cgggaacagc gccaggcagg     60
tcgcgccggt cagcagcggg tagccgatcg gcggcgggat gatcgccagc ggcgtgaaca    120
gcaccgcgga aacggcggg taggtgtagg cagcgcgcc gccgatggtc gagacgggca     180
gctccgagta gatcgagtgg cccttgagga acgtgtccgc gcccagccgg tagatgtcga    240
cgtcggtcgg ccacttccgg atgccgtgcg cgtagtacgc gagcgcggcg aacaggccga    300
cggccagcag gagttccaag cccaggcgta cccgctcggc ggtactgccg tacctcatcg    360
tctcgatgac agctttcact cgttctccca gtcccggcca ggcgtgatct cacggaacag    420
acgccgcaac gcctatcttc gttgcccgcg tgatcgatgt tacgagcggg tcccccttgc    480
gctacgcgcg gctgcggtcg gtgaacacga tccagcgaag cacgctgtag aggaacaccg    540
cctccaacgc gccggcgatg atgcgcgcca ggtggtactg cacgcccagc gcggccaggc    600
cggcccggc gccgaggatg aacgcgaagt agttgaccgc caccgcgatc gcgtagagca    660
cggcctgccg cccgaccgga gcgtgcgagc ggaagttgaa gacgcggttg agcacgaagc    720
tcagcgcgaa ggcgcagacg taggccacgg tgatggcgac cggcagcggc agcccggcca    780
cgccgtggcc cagggtcagc agcagcaggt cgacgccgaa ggtgaacccg ttgatcagcg    840
cgaagcccac gaagctgggc gggaccagcg tgttcagccc gaagggcagg taccggacga    900
ccgtcgcgca gaacgacgcg aacctctcca cgagcgaccg cgtcacccgg atgtcctgtt    960
gcacggcgcc acggtggcag aaccgggtga cgggaaggtg agcagccggt agtcaacagg   1020
cggcggaaag tgtcaccgac cccacggaga tcacacttcg ggctgatatc ttcttgtgac   1080
cccgtccgtg tgatcctccg tccccgcgcg aggcgcgcgc cgccccgaag cccccgtca    1140
ggaggcgcgg atgttcgcct ggttctgggt gacgctcggc gtcgccttcg gctcggcgat   1200
cgtgcccgtg atcagcgtcg aggtgttcgt gctgggcctc gtggccagcg agccggggct   1260
gcactggctg ctgatcggcg cggccgtctc gatcggccag atcgccggca aactgctgta   1320
ctacctggcc gcgcgcggat cgatcaggct gccgcggttc ctgcacgacc gcctgcaccg   1380
ggagcgcccg cccagccgcc gccgcgaccg gtggcaccag cggaccaagt ggctgcgcgg   1440
caaggtggag gccctgcgcg agcgctgcca ccggcacccg cactggatga cgggcaccta   1500
cggggtcagc tcgctgatcg ggctccccc gttcatggcg acgaccgtgc tggcgggcct   1560
ggccgacatg cggatgtcga cgttcctcac ggcgggcctg accgggcggt tcatcaggta   1620
cagcgcgctg gccgcgtgcc cggcggtgtt cgcgggctgg ttccaccact gagctcgggc   1680
taccggagga gccggaacag cccgtcggag gggtccacca cgacggcgag ggattcgccg   1740
gccgtcggga cccggtggct gggccgcgg tgggtcacct cgtgtcggtc tgcccgccgg    1800
tctcgcacgg cgggcgcaga cgaccagcgc ggtcgcgggc cggccgccgc ttaccccggg   1860
caccggccct acggcacgac ctcgtcgaag ttcccggcgg aggcgggtgt cgaccggccg   1920
cgagtgagtt tggcgccaca cgtgccggag gcggctgcgt tccgacaaag tggaccgcat   1980
gagataccgg cttttcgggc gcaccgggct gcgcgtggcg gagatgttcc tcggggcgat   2040
ggcgctgcag gaaccggacg aggcgcgcg ggtggtcaag gcctacgccg acgcggggg    2100
caacgtgatc gacacggcct cggcgtacgc ggagagcgag aacgtgctgg gcgaggtgct   2160
gaccgaccgc gaccggttcg tgctggccac caagtacacg ctgacgcggg atccgcacga   2220
cccgaacgcc gggggcagcc accgcaagaa cctggtcgcg tccctggagc gcagcctgcg   2280
```

```
gcggctgcgc accgactacg tcgacatcct gtgggtgcac acgtgggacc cgcacacgcc    2340
ggtcgccgag acgctgcgtg cgctggacga cctggtgcgg gccgggaagg tcaggtacct    2400
cggggtgtcc gacacgcccg cgtgggtggt gagccgggcc gacgtgctgg cggagtggcg    2460
cgggtggacg ccgttcgccg gggtgcaggt gccctacagc ctgctgaacc gcgacatcga    2520
gcgcgacgtg ctgccgatgg ccgagcagct ggggctgacc gtcgcggcgt ggggcgtcct    2580
ggagcacggc gcgctgaccg ggtccagccg ggtcggttcg ccgtcgccgg agcagcagcg    2640
ggtggcggcg gcggtgcgcg cggtggcgga cgagctgggt gtcacgccgg cacaggtggc    2700
gatcgcgtgg tcgcgggcgc ggtcggcggt cgtgcacccg ctgatcgggt ccggacggc    2760 ggaccgggtc gcggagagcg tcgccgccct ggacgtgacg ctgcccccgg aagcggtggc    2820
gaagctggag gcggcggcgc cgttcgagcc gggcccgttc gccgacttcg tgaaccagtc    2880
ggcggccagc gccggggtgt tcggccacgg cgaggtggtg gcgcgtcagc tgcgggagtg    2940
aggcagctcg gcgacggcgg cgacggtcca gtgcgccggt ttcggcgcct cgccgggcgg    3000
caggcccagg atccaggtca gcacggccga tgccttggcg tgggtgccga gcagtcccca    3060
ctggttgagg cggacaccgg cgtccgcctc gtagccgtgg cacagccacg agtgcacgtc    3120
catcaggtcg aagtccgcgc cgatgatctc gaagccacgc aggacggcgc gctccggcat    3180
cggcgcttgc tgtaggagtt gggccagcgg ttccgccttg gccgggtcca gctcgccgcg    3240
gaccgcctcg acgagcgccg cggcgtcgcg gcggtgaag ccgatcgcca gcaggtgccc    3300
gtcgaaccgc gccgccgcgg ccgggtcggc gtgccaggcc cagaactccg gccgtggtc    3360 gacaccggta aggcacctgc tcaggctgat gaacgactcc ggcaaccacc gcgattgcca    3420
cccttcccgc gcgggacgcg ggacggccag gtagcccgcg agcaggagtt cgtcgtccac    3480
ccgcacagtg tcgcagcgcc cgcaccgggt tcgcgacgga ttaaggatca gcgcccggg    3540 gtcccggttc tctgggcggt tgccatccac cggtcggcga gcgtgccgcg ctgcgcgaac    3600
cgcctcgggc gtgggttcgc gttgcgcgtg cgccaaccgg caccgccgcc agtcctccga    3660
gtgcacgcac cgcgggcgcg gcaccaccta acgcgcggcc tccgccgctt ccaggtccag    3720
cgccttgcgc atcgtggcgc gggcgcggcg ccggtcgccc gccaggtcgt acgcgtgcgc    3780
caaccggtac cagtaccgcc agtcctcggg gtgctgctcc agctccgcgc ggcgctcctc    3840
gaaccacgcg tccgccgcgg cgcggtccac ccggccggac gggcggcgcg caggtcgtc    3900 gacgtccggc agcccgccct cggcgtccag ccgtcgcgcc aggtgctgga tccgcgtgcc    3960
ggaccgccag gtggcgacga ccatccacag ccccagcagc ggcagcacga gcacgccgac    4020
accgagcgcg atgcccacgc cggtgccggt cgcgatcagc tccacccccgc gcgccccgag    4080 cagcaccagg tagaccacca gcgcggcggt catcaccagt gcgacgttgc gggccttcac    4140
aggtcgagca cgttctcgag gccgacggtc aggccgggac ggcccagcac ctcccgcacc    4200
ccgagcagca caccgggcat gaacgaggtc cggtccatcg agtcgtgccg gatggtgagc    4260
gtctcgccct cctggccgaa caggatctcc tcgtgcgcca ccagcccggg cagccgcacc    4320
gagtgcacgt gcacgtcctc gaccccgcgcg ccgcggggcgc cgtccagttc gctcgtcgtc    4380
gcgtccgcgc ccggcttcag cccggcctcg cggcgcgcct ccgagatcag ccgcgccgtg    4440
tgggccgccg tgccggacgg ggcgtccgcc ttgcggttgt ggtgcagctc gatgacctcg    4500
accgactcgt agaaccgggc cgcctgctgc gcgaaccgca tcgcgagcac cgcgccgagc    4560
gcaaagttcg cgcgatcag caccccgacc tccggcttgc ccgccagcca cgagcgcacc    4620
gtctccagcc gctcctcgct gaacccggtg gtgccgacga ccgcgtgcaa cccgttgccc    4680
```

```
accaggaact ccaggttgcc catcaccgcg tccgggtggg tgaagtcgac gaccacctcc    4740
gcgccggcct cggtcagcgc ggtcaggtcg tcgcccgcgt ccagcttcgc cacgaccgtc    4800
atgtcgggcg cgcccccggc ggccttgacc acctgcgcac ccatccgtcc ctgggcgccc    4860
agcacgccga cccggatcgg gttgtcctcg ccgcgggggt tcatttcgcg atcacctcgt    4920
gcagatcttc cggtaggtcc tgctcggaag cgtacggccc gaccaccgcg gcggcggtga    4980
cccctcccgg cgtcccgaac agggtgcggg ccagctcaca cacctcctcg gtggtcaccg    5040
cggcgatccg ctccaccgac tcgtcgacgg tgaggtgcac gccgtagttg agctcctgct    5100
tgccgatgcg cgacatccgc gacgcggtgt cctccaggcc cagcacgatc ccgccgcgca    5160 gctgccccatt ggcgc                                                    5175

<210> SEQ ID NO 12
<211> LENGTH: 4408
<212> TYPE: DNA
<213> ORGANISM: Amycolatopsis sp.

<400> SEQUENCE: 12
gcggcacacg cctcggcgcc ccggccgcct gcgccgcggg gctgggcggt cgacgacgcc      60
tgccacgcac aggtagtcgg gctggaggac tattagttac gcggacatgc gaaaagggcg     120
ccggtcgaag ctcgaccggc gcccttcacg tgtactggct cagtgaaacg agtcgccgca     180
ggcgcaggag cccgtggcgt tcgggttctc gatggtgaag ccctgcttct cgatcgagtc     240
gacgaagtcg atcaccgcac cctcgacata cggcgcgctc atgcggtcga ccgccacgcg     300
caggccgtcg aagtcgcgga acaggtcgcc gtcgagcgtg cgctcgtcga agaacagctg     360
gtagcgcagt cccgcgcaac caccgggctg gaccgcgatg cgcaggtgca tgtcgtcgcg     420
gccttcctgc tcgagcaggg ccttcgcctt gctcgccgcg gcgtcgctca acgtgacgcc     480
gtgggtggcc tcggcctcgg cctgcgtgct ggtctgctca gcggcagtca tagctctccc     540
tcggggtctt gccgtgcacc gggtgggggg tgctcctccc tactggaaca ccggtgccac     600
ccgatctgtt cccgggctgg ttcccgcctt ggcgctgatc ccatggttac acatcggcga     660
gggggttgaa cacgcacgcc gctgtctgga ataagctggt tgggtgaggt ttctccgtcg     720
taacagcacg accaccgcag acagccccga gatcgaggcg gccgaggtgg ccgaaagcgt     780
cgaatctcac acccgtggct acaccccggg caagggcagg ccgacgccga agcgcaagga     840
ggccgagggc aagcgccgcg gccccgtcgc gccccgccg aggaccatgc gggaggcgat     900
gaagcgcaac cgcgagctgc gcaagtcgaa cccggtggac aaggaagagc gccgcaggct     960
cgccaaggag cgccaggagc ggatggccgc gggcgacgac cgctacctgc tgccgcgcga    1020
caagggcccg gtcaaggcgt acgtgcgcga cctggtcgac tcgcgccgcc acttcctcgg    1080
cgcgttcatg ccgctggcga tcctcgtgtt cgtcgtgctg ctggtgccgt accggtgat    1140 ccagcagtac gtgacgctgc tgtgcatggc cgcgctgctg gtcatggccg tcgagggcta    1200
cttcaacggc cgccgcatcg cgcggctggc cagggcgaag ttcccgaagg agaacatcag    1260
cggccggtcg ctgggctggt acgcgttcgt ccgggcgagc cagatccgca agctccggat    1320
gcccaagccg cgcgtgaagg tcggcgacac ggtctcctga ccggctggag cgcactccag    1380
gtcgttagca aggcgaacca tttccggtag gctgccggac atggagtttc gccgtctcgg    1440
ccgcagtggc ctgtccgtca gtgagatcgc ctacggaaac tggctcaccc acggttccca    1500
gatcgacgag gaccaggccc aggcctgcat caaggccgcg ctcgacgcgg gcatcacgac    1560
```

```
cttcgacacc gccgacgtct acgccaacac cctggcggag tcggtgctcg gccgcggtct    1620
ggccggtcag cgccgggaga gcctggagat ctgcacgaag gtgttctggc cgaccggccc    1680
cggcggcccg aacgaccgcg ggctgggccg caagcacatc atcgagtcct gccacgcctc    1740
gctgaagcgg ctgcagaccg accacatcga cctctaccag gcgcaccggt tcgacccgac    1800
cgtgccgctg gaggagacca tgtcggcctt cgccgacctg gtccgccagg gcaaggtgct    1860
ctacatcggg gtgtcggagt ggaacgccga ggagatcacc cgcggcgccg cgctggcccg    1920
cgagctgcgg atcccctccg tgtcgaacca gccgcagtac aacatgctct ggcgcgtcat    1980
cgaggcgcag gtcgtgcccg ccagcgagcg cgaggggctg agccagatcg tctggtcgcc    2040
gatcgcgcag ggggtgctga ccggcaagta caagcccggt cagccgccgc ccgccgggtc    2100
gcgcgccacg gacgagcggg gctcgcagtt cgtgcagcgg ttcctgcggg acgaggtgct    2160
cgagcgcgtg gcccggctgg agccgctggc cgcgcaggcg gggctgacgc tggcgcagct    2220
ggcggtggcg tgggtgctgc agaacccgaa cgtcgcctcc gcgatcgtcg gcgcgtcgcg    2280
gccggagcag gtgcacgaga acgtgaaggc ggcgggcgtg aagctcgacg ccgacctgct    2340
gaccgagatc gactcggtgc tgctgggcgt ggtcgaggac gatccgcgcc tgaccgctcg    2400
cgccggctga cgataggttt ggcgccgtga ctgacgtgtc gttcgccgat gtcccccagc    2460
ccgacgaagc cgcccgcgcc gaggcagtgc ggcggcacgc ggagctgctc aaaccggtgt    2520
ccgcgctggg tgagctggag cgctcggcg cgtgggtcgc ggcctgccag ggctcggcgc    2580
cgccgcggcg gttccagcgg cccgggtga tcgtgttcgc cggggaccac gggatcgccg    2640
cgaagggcgt ctccgcctac cggccggagg tcaccgggca gctggtggac agcctgctca    2700
agggcgccgg gccggtcgcg gtcgccgccg cggtggccga cgccgggctg cgcgtggtgg    2760
acatcgcggt ggacgaggag acgccggtcg ccgagtacaa ggtccgggcg ggctccgggt    2820
cgatcgacgt cgaggacgcc ctcaccgacg acgaggtgcg ggccgccctg cgggccggca    2880
tggcgatcgc ggacgccgag gtggacgagg cgccgatct gctggtcgcg ggcagcgtcg    2940
gggtcggggc gaccacaccg gccgcggtgc tggtcgccgc gctgaccggc gccgagccgg    3000
tggccgtggt cggccgcggt tcgggcatcg acgacaacgc gtggatgcgc aagaccgtcg    3060
cgatccggga cgcgctgcgg cgggcccggg cggtgctgcc cgacccggtg gcgctcctgc    3120
ggaccgcggg tggcgcggac ctggccgcgt tgaccgggtt cctggcgcag gccgcggtcc    3180
gccgcacccc ggtgctgctg acgggctcg cggtcggcgc ggcggcgctg gtggcggagg    3240
aactggcgcc cggcgcgcgc tcctggtggc aggccgcgca ccgcgacgcc gagcggcgc    3300 accagatggt gctggagcac ctcgacctca agccggtcgt cgacctgggc atccgcctcg    3360
gcgacggcac cggcgccgcg acggccctcc cgctgctgat cacggccgcc cggctgctca    3420
cggacctgcc gacgcacgcg gaagccgggg tcacgccgcc gaacgcttga tcctgacgcg    3480
acgtcaggtc ctagcgtcgt ccacaccggc gcaaaagcgc tggtggaagt gggtgaacgg    3540
catgttctac aaggtcggcg agctggcacg ggcgaccggc ctgacggtgc ggacgctgca    3600
ccactacgac cacgtgggtc tcgtgcgccc gtccgggcgg acgcactccg ggcaccggct    3660
ctacgacgag tccgacgtcc ggcggttgta cgaggtgctg gccctgcggc agctgggcct    3720
gccgctcgag gacatcggcg cggccctgga gggcacgtcc gacctggccg agctgctcac    3780
gcggcaccgg gaccacctcg accggcagct ggtggcgatg cgcacgctcc gcgcgcacct    3840
caccacgatg ctggcggccg tcgacgaacc ggcaggcgtc accggcttcc tggctctgat    3900
ccgggaggtg accaccgtgg acgagacggt gaagcagtac ttcagcgaaa cccagctggc    3960
```

```
ggagctggcc gagcgccgat cgcggctcgg cgagcaggag gacgtccagc ggaggtggca   4020
ggacctgatc ccccgcgtgc agctggccgt cgagaccggg gtcgacccgg cgtcggcgga   4080
ggggcgggcg ctcgcggccg agtggatggg cctgctggag gctttccacg gtggcgacac   4140
cgggctgcgg gactcgctct accgcatgca ggcggacaac agcgagcgga tccagcgtga   4200
gcacggcggg ccgtcgccgg agcagctgga gttcatccgg cgcgccagcg cctcgtgacg   4260
acgaagggcc accccgccgg aacggggtgg cccttcatgt cgaagtgatc aggacagctt   4320
gtgcatccag ccgtgcgggt cggggcgtgt gccctcctgg atgccggtca gttcggcgcg   4380
cagcttcatc gtcacctcgc cgggctcg                                     4408

<210> SEQ ID NO 13
<211> LENGTH: 4911
<212> TYPE: DNA
<213> ORGANISM: Amycolatopsis sp.

<400> SEQUENCE: 13
ccgaagtgct cgtcggcgat ccggtcgaac gggggcagac cgtagggcag gtcgctcgcc     60
tgcgagaacg ggttgtccgg tgtcatccag cgcggcccct ctgtcctgtc gaccctccga    120
tctccgcgtc ggaggacgtc ttcttcttcc taccgcgctt cggcgccggc ggcaccaccc    180
cggccagatc cgcactgtgg tcgttgacgc gcaccacgaa cgggcgcacc tcggtgtagc    240
ggaccacgga gatcgacgcc gggtcgacca cgatccgctg gaacgcgtcg aggtgctgcc    300
ccagcgcgtc ggccaggatg gacttgagca cgtcgccgtg gctgcacagc agccagacgg    360
cgtggtcgcc gtgctcggcg gtgatccgcg cgtcgtgctc gcgcaccgcg gcgaccgcgc    420
gggcctgcat gcctgccagg ccctcgccgc cggggaacac cgcggccgag gggtgggcct    480
gcacgacccg ccacagcggt tccttgacca ggtccttcag ctcgcggccg gtccactcgc    540
cgtagtccac ttcggacagg cgcggttcga cggtgcgggt gaggcccgc tcggcgacga    600 gcggggccac cgtgttcttg cagcgcagca tcggcgagca cacgacctcg gccagcggca    660
cgccggccag ccgctccacg agcgcctgag cctgcgcgcg gccggtgtcg tcgagcccga    720 ccttggggt ccgcccggcc agcacgcccg acccgttcgc ggtcgagcgg ccgtgccgaa    780
gcaggatcac ggtagccacg ccgccaacct acatggcggg acccgcgttc ggatcaagga    840
cgccggtggc gaccagcacg atgagcagca cgccgagcgc gatccggtag atcacgaacg    900
gcacgtagct cttggtcttg atgaagttca tcagccatgc gatcaccagg tagccgacgc    960
cgaaggcgac cagggtggcc aggatcgtcg gcccccactg cgggctgtgc tcgccaccga   1020
tgtcggtgag cttgtacagg ccgaggcga agaccgcggg cacggccagc aggaacgcgt   1080
actcggtggc gtcggcgcgg gtgtagccga ggaacaggcc cgcggtgacg gtgccgccgg   1140
agcgggacac gccggggatc agcgccatgg cctgggcgaa gccgtagccg agaccatgcg   1200
ggacggtgag gtggtccagc gtccggtact ggcggcccac ccgtcggcg atgagcagca   1260 ggatgccgaa cccgatcagc gtcgtcgcgg tgaggcgcag gtcgcggaac gcgctgtcga   1320
tggcgtcctg gaacagcagg ccgagcaccg cgatcggcag cgaccgacg atgatcagcc   1380 agccgaggcg ggcgtccggg tcgtggcgcg cctcccgctg gtagagcgag cgccaccaag   1440
cggccaggac gcggccgatc ttcttcgaga agtagaggat gaccgccagc tcggtgccga   1500
tctgggtgac cgcggtgaac gccgcgccgg ggtcgtccca gccggcgagc gccgcggtga   1560
tgcgcaggtg ggcgctggag gagatgggga ggaactcggt caggccctgg accaggccga   1620
```

```
ggacgagtgc ttcgaaccag cccatgctca ccgggccttc ggggaaatca gtcgcgttcg    1680
cacggtggga gaggctatcg gcggcgcgga tcactcgatg agccgccttc gtcaagttct    1740
ttacagtact ttcgttacgc ccgcccgtcg cccaccgcca ccctcaacgg tggcgctccg    1800
cgccgcagct acgccctccc gtctcccacc gccaccctca cggtggcgc tccgcgccgc    1860
agctacgccc tcccgtctcc caccgccacc ctcaacggtg gcgctgcgcg ccgcagctac    1920
cccctcccgt ctcccaccgc caccctcaac ggtggcgctc cgcgccgcag ctactctctg    1980
tgcatgcaga agcgacagct gggcaggtcg gggttgcggg tctcccggat ggcgctcggc    2040
acgatgtcct ggggcgcgga gaccgacgcc gacgaggcgg ccagccagct cgtcgcgttc    2100
gtcgaggcgg gcgggacgct cgtggacacc gccgacatct actccggcgg cgagagcgag    2160
cggatcctcg ggggcctgct gggcgacctg gtgccgcgtg acgagatcgt cgtggcgacc    2220
aaggccgtcg cccggcgcac cgacgggccg ttcggcgggg gcgcctcccg cggcgcgttg    2280
ttgtccgcgt tggaggggtc gctgcggcgc ctcggcgtgg accacctgga cctgtggcag    2340
ctgcacgcgt gggacgactc ggtgccgctg aagagacgct gtcggcgct ggaccacgcg    2400
gtgacctcgg gcaaggtccg ctacaccggg gtgtgcaact acgcgggctg gcagctggcc    2460
tcggccgcgc cggcccggcc ggccgggctg gtcgccacgc aggccgagta ctcgctggtg    2520
gagcgcgggg tggagcgcga gctggtcccg gcggcccgcc accacgggct cggcgtgctg    2580
ccgtgggcgc cgctgggccg ggggtgctg accggcaagt accgcacgg cacgccggcc    2640
gactcgcggg gcgcgtcggc cgagtacgcc ggctacgtcg agcagcaccg caccgagcgg    2700
gcggcgcgga tcgtcgaggc ggtcgccacc gcggccgacg gctgggggt gtcgccgctg    2760
gtggtggcgc tggcgtgggt gcgggaccgg ccgggcgtgg tcgcgccggt ggtcggggcg    2820
cgcgacaccg gcagctgac cgggtcgctg gcggcggagg agatcgccct gccggtcgcg    2880
atctcctcgg cgctggacga cgtcagcgcg gtcgagttcg gttaccccga gcgggcacg    2940
aagtgaccgt ggggtggatg gcacgtgacg cggcggggtt ttcaggggat gctggaggaa    3000
acagaggaat gcgatccgga ggtcttgtgc gctcctccgc caccgtcggg accggtgtcg    3060
tgctggtctg cgccctggtg ctgagcgggt gctcgtcgaa gtccggtgac tccaccgaca    3120
cgctgcaggt cgtggccgac ccggtcgcgg cgacggcgcc cgtgtcgccc cagcctgccg    3180
ccgcccccgc gggcaccgtg atcgcctccc ccgagatcac cgcgctggcc gccgaccccgg    3240
ccaccgggac gctggccgtc gccgtgccgg acgccgtgct gctgtaccag gccgctgacc    3300
tggcggccgc cccggtgcgg gtgccggtcg cgggcgggc cgagcacctg cgcgtgtccg    3360
gcggggtgct gctggccacg ctccccgcgg ccgggcaggt cgcccggatc gccttgcccg    3420
gcggcgaggt gagcaccctg gccgtggccg gtcagccggc cggcgcggtg tcgagggcg    3480
accggacggt ggtcgcggtg cgggaccgca aggccgtgga cgtgttcacc ggcgaccagc    3540
tgaccaagac gatcgagggc cagctctaca gcgccgacga cgtgctgcag gccggcggga    3600
acaccgtcgt gctggacgag ttgcgcaccg ccgtgttctc ggtggacgtg gacggcggca    3660
ccgtggccga gggcctgcgc gccggcgacg gcgccaccaa cgcggtcgcg gactccttcg    3720
gccgggtgct cgtggtcgac acccgcgccg gtgcctcct ggcgttctcc accgcccgc    3780
tgttgctgcg gcagcggtac ccggttcccg gcggggcgta cggcctcgcc tacgacgcgc    3840
agcgcgcgct ggcgtggtg acgctcaccg agcgcaacga ggtcgtcggg ttcgacgtgc    3900
gcggcggcga accggtcgag aagtaccgtt tcccgacggt ccggcagccg gattcggtta    3960
ccgtcgagga gcggagcggg cgggtggtcg tcggctccgc ggcgggagaa ggggtccagg    4020
```

```
tgatccagcc atgaagcacc aggaggcggt ggtcgacgag gactgggagt accgccggtt    4080
gcagttgcca cccggcgtct cccggcgggc cgcggccacg cagctgtcca tcaacgccga    4140
gtacggcggg tgggagctct cgacggtccg gctctactcc gacggcaccc ggcgggtgtg    4200
gctgcgccga aagcggcagc cggccaccgc cctgcccgag gtcctgatct gacccgagcg    4260
gcgcccgcag ctgggcgccg ggccagagcc cgcccctcg acggatgcgc tacgcgcgaa    4320
gagcggtaac gggtggggcc ctcgtgtcga tctcagtgct gccccttgga aggagcagca    4380
tgtcctcctc gcccgttgtc cgtgtcgtga ccgccgcctg cgccggggtc gcggtggccg    4440
tggcgttgct ggcggtcttc gccgggatgg gcgtggcgct ggtggtgctg ctgggcatcg    4500
tcgcgctggt cacatgcgtc ccggtgtggt tcgcgccggt gttgctcgcc gccgccgcg    4560 gtgtggccga cgtccggccg atcgcggtgt tcaccctcct ggcggggtgg tccctcatcg    4620
gctgggtcgc cgcgctgatc tgggccggcg cggcgcgcgc ggaagccggg ccccgcccgg    4680
tcgggaccta gcccgcgagt gagcggcccg tctcctcgag cgcttcgcgg aggatgcgca    4740
cggctttggg gcccatgccg tgcagggtga gcagctcggc ctccgtcatg gcggcgacct    4800
ggtcgagcgt ggtgatcccg gcgttgccca gcgcgcgggt ggcggggcgg ccgatggccc    4860
gcggcaggtc gccgctctcg cccgccaccg ccgcggtggc cgtgcccgcg a             4911

<210> SEQ ID NO 14
<211> LENGTH: 4872
<212> TYPE: DNA
<213> ORGANISM: Amycolatopsis sp.

<400> SEQUENCE: 14
acgtcaaccg gaacgggttg caggaccagg gcgagcccgg catcgccgac gtgggcgtgc      60
ggctgcagaa ggccgacggc accccggtcg ccgggacgag caccggcccg cacggccagt     120
accagttctc gcacctgccc gacggcagct accaggtctg cttcgacacc gcgaagctcc     180
cgccgcagta cggcgactac cagctcacca ggcagcgcgc gggcgcgccg gccaggact      240 ccgcgcccga cccggccacc ggctgcaccc cgccgaccga gctgaccccg agccgtaccc     300
aggacttcac gatggacgcc ggcctggcgc cgccggtcaa ccggatcgcc gcgctggtct     360
ggcaggacgt cgacggcgac ggcgcgccgg gagcgctgga gccggggatc gccggggtgc     420
cggtgaagct cgcgcggcgcg gacggcaccc aggtcgccat gaccaccacc ggccaggacg     480
ggaagtactc cttcgacgac ctgccgtccg gctcgttcgc ggtgtgcttc gacctggcca     540
acctgccgca ggccgcggcc gacttcacgc cggttgaggg gagcccggtc tccggcgccg     600
acccggcgac cggctgcacc ccgcaggtga ccctcggcct cggcaagcgc gaggacaccg     660
cgctgaacat ggggctcgcc gcgcctgcca accggatcgg cgaccgggtg tgggcggaca     720
cgaaccgcaa cggcatcgcc gacgccaccg agtccggctc gagcggggtg ccggtcaagc     780
tgctccgcgc cggcggcggc gaggaggcgt cgacgaccac cggcgccgac ggccggttcc     840
ggttcaccgg gatcccggac ggtgcgtacc aggtgtgcgt cgaccgcgcc gcgctgcccg     900
cgccggtggc cgggtaccag ttcacgaagc cgcgcgccgg tgagtccaca aaggattccg     960
atgtggacct ggcgagcggg tgcgcccgc cggtcgccgt cggcgtcggc caccgcgacg    1020
agagcaccat cggcgtcggg ttgtcgcccg cgcgcaaccg gctcggcgac ctgctgtggg    1080
tggaccgcaa cggcaacggc acgcaggacg cgggagagcc cggcgcggcc ggggtcccgg    1140
tgacgctgac cgacgacgga gggcgcccgg tggcgaccac ccgcaccgcc gcggacggct    1200
```

```
cgtacctgct cgacgacctg cccgacggct cgtaccgggt gtgcttcgac ctcgccggcc   1260
tcgccccgga gttccgcggc ttccacatcg caggcggcga cccgggctgc gccgaccgg    1320 tgaccgtcgg cccgaagccg cgggaggacc tgtccgtgcg gatcggcctc gtcagcgcca   1380
gtccggcggt cgtgcctgcc gcgcaggagt ccacgagcgg cggcgggttc cccgtcgggt   1440
gggtgttgtt cggtgtcgtg gcggcgatcg gcgcggtcgt cggggtgcgc tggtggaagg   1500
ccgccgagcc gggagcgtga cccggtagtt tgggcgttat gagaattctg cgggtgctcg   1560
gagtcgtcgg gatggcggtc gtgctggccg gttgtgcgga agccgcggag acggcggacc   1620
gggtgagcgc gtgctcgcag gccctcgggc tggcgaacct caacccgtac gcctcggcgc   1680
aggaggtgtc cgcccaggcg cagcagaagg ccgaggagct gcgcaacctc ggcaaccggg   1740
tggccgacca gacgctgcag cagaacctgt tcgcgatcgc cgactcctac gtcgcgctgg   1800
agcagcgcaa gtcgcagggc ctgtccgacg tgaacgactg ggtccagacg aacaccgcca   1860
acctggagcg gctgcgccag gcctgcacgt gaggcggcgg caggccggct gtccccggga   1920
ctcctaggat cgccggggct ctgcctgttc cgcggcgcgc ggggatcgt ggagcccgaa     1980 caagccgaga agggatttcc atgacagcga acacactggc cggcggcacc ttcaccctcg   2040
caggcgggct caccgtcggg cgcatgggct acggcgcgat gcagctggcc gggcctggcg   2100
tgttcgggcc gcccgcggac cgggacgccg cggtcgcggt cctgcgcgaa gcggtcgagc   2160
tgggtgtcaa ccacatcgac accgccgact tctacggccc gcacgtgacg aaccagatca   2220
tccgcgaggc gctgcacccc tacgacggga tcgtggtggt gaccaaggtc ggcgcggtgc   2280
gcgacgacca gggcgcctgg gtgcaccagc gctcgccgga gcagctgcgt gcccaggtgc   2340
acgacaacct gcgcaaccte ggcgtcgacg cgctcgacgt ggtcaacctg cgcgtcggcg   2400
gcggggacga cggccactcc gcggtgcccg gctcgatcgc cgagccgttc accgcgctgg   2460
tcgagatgca gcaggagggg ctgatcaagc acctcggcat cagcacggtc aacgccgagc   2520
aggtcgccga ggcgcagtcg atcgcgccgg tcgtgtgcgt gcagaacgcc tacaacgtgg   2580
cccaccgcga ggacgacaag ctggtcgagt cgctggccgc gcagggcatc gcgtacgtgc   2640
cgtacttccc gctcggcggg ttctcgccgc tgcagtcgga ggtgctgaac tcggtggccg   2700
cccgcctcgg cgcgaccccg atggccgtcg cgctggcctg gctgctgcag cggtcgccga   2760
acatcctgct catcccgggc acgtcgtcgg tcgcccacct gcgggagaac gtggccgccg   2820
cgtccctgga cctccccgcg gacgcgatcg ccgaactcga cgcgatcgcc taacgcacca   2880
cgaggtggag cccccggccg gccgtctccc ggtcgacgac cgtggtctcg ttccagccgc   2940
ggggccgccc ctcgaacagc agggcgcgga cccgcggcag gcggcgcagg tgacggcaga   3000
aggacgcctt gcgcagcacc cggccgcgcg cgcgttgccc ggccagcgcc tccgccgggg   3060
tgcagtccac ccacagcagg tgccgccgcc gtccggtgag cagcccggtc agcatcagcc   3120
acgccctggt cgccgcgccg atggccgggt cgtgcacaac gaccgggccg ggcgtgcgga   3180
tcgccgcgag caccacccgc agccggtgca ggacgtgcac cgccgggcgg tagcggcggt   3240
acggcgtgcc gggcggcagc gcggcggcca gccggtcgcg catctggtcg gagtcgagca   3300
cctcgaccgg gcggctggcc tgcgtgctgc gcagcagcgt gctcttgccc gaaccgggca   3360
gcccggcgat gaccagcagc gcgcgcggtt cgatcgtcat ctgcaaggtg gcgccggctg   3420
tgctgtccat accgggccaa cgcgcgatca cgccacccgc gttccgcact tacaggtcaa   3480
atcggtcatt cacagcggcg ccacagccgg gaccctggcc gagcggcggc gcagcccgaa   3540
ggccaccgcg gcgaagccga gcccgaacag gcccgccgcc gcgaagcccc agccggggcc   3600
```

| | | |
|---|---|---|
| ggtgtggtcg atcacgaacc cgaccaccgg gctgcccgcc gccatgccga gccgggtggc | 3660 |
| ggcgtcgagc aggcccatcg cctcgccgcg cacccgtggc ggcgcgaggc cggtgacctc | 3720 |
| ctcggcggtc gacgcgagcg tcggcgcgca ggccaggttc gtcggcacca gcgccagcgc | 3780 |
| cagcagccac cacggcagcc cggtggccaa cccgaccggg atcacgagca cggtcagcag | 3840 |
| caccatcagc cgcgcctgcg acagcgactt ccgcaccgcc ccgtgcacga tcccgccgac | 3900 |
| cgccgaggcg acgcacatca cggcgatcac cacgccggtc cagcccacct cgccggtggc | 3960 |
| ccgcagcgcg gcgagcgtcg ccagttcggt gcccatcagg cagaacagcg ccccgacgc | 4020 |
| gacgagcagg gcgccgacca gccgcgggct gagccactcc cgcatcggcg gccgctcggc | 4080 |
| ggtgaccgtc tcgccctcgt gccggatcgg cgggttgaac cagcacagcg cgagggtgcc | 4140 |
| gagcgcgaaa cagacgccga tcccgctcag cgcgacggtc gaggacagct gcgtcgacag | 4200 |
| ggcgatgccc gcgctcgggc cgaccatgaa gctcgtctcc agcaggatcg agtcgagcga | 4260 |
| gtacgccgag cgccgcgact ccggcggcac cagcgcggtc agcacctggc gggcgatcga | 4320 |
| gctggcaggc agcacgagcg cgcccgccgg cagcgcggtc acgagcagcg ccgcgtacgg | 4380 |
| caggtgcggg gtggccagcc agaacgccgc ggaggtcagg ccgcacaccg aggtgaccgc | 4440 |
| gcgcagcccg tagcggtcga tcatccggcc gacgaccggc gcgccgatgg cgctgcccag | 4500 |
| catcgtcgcg gtcccgacga gacccgcctg gccgtacccg cggccgaggt cgctgacgac | 4560 |
| gtgcagggtc agcgtgatcc cggtggcggt catcggcagg cgggtgaaga agaacagcag | 4620 |
| catcgccatg cggaccccgg gcagggcgag gacctggcgg tacggctgga gggacatgct | 4680 |
| cccactttgg cacggccgtg caactccttt tcgcgccgct tgccgctccg gaaaactgac | 4740 |
| agttactatc aaaaagtagt gactatcagt ttggaggctg ggatggacgg gtcgaagcgg | 4800 |
| tggtgggcgc tgggtgcgct ggccgtggcg ttgctggcgt tcggactcga tgtgacggtc | 4860 |
| ctgtcggtgg cc | 4872 |

<210> SEQ ID NO 15
<211> LENGTH: 4821
<212> TYPE: DNA
<213> ORGANISM: Amycolatopsis sp.

<400> SEQUENCE: 15

| | | |
|---|---|---|
| gcggcagatc gagcagatcc gcgacgcggt ggaactcccg ttcctgcacg ccgacctcta | 60 |
| ccgggagtac gagctgcggc cgcccaaggg cgtcctgctc tacggcccgc ccggttgcgg | 120 |
| caagacgctg atcgcgaagg cggtggccaa ctcgctggcc aagaaggtgg ccgaggcacg | 180 |
| cggggacggc gactcgaagg acgccaagtc ctacttcctc aacatcaagg gcccggagct | 240 |
| gctcaacaag ttcgtcggcg agaccgagcg gagcatccgc tgatcttcc agcgggctcg | 300 |
| ggagaaggcc tccgacggca cgccgtgat cgtgttcttc gacgagatgg agtcgatctt | 360 |
| ccgcacccgc ggcagcggcg tctcctcgga cgtggagacc acgatcgtgc cgcagctgct | 420 |
| ggccgagatc gacggtgtcg aggggctgga gaacgtcatc gtcatcggcg cctccaaccg | 480 |
| cgaggacatg atcgacccgg cgatcctgcg gccgggccgg ctggacgtga agatcaagat | 540 |
| cgagcggccg gacgccgagg gtgcgaagga catcttctcc aagtacctga cgccggggct | 600 |
| gccgatccac gccgacgacc tgccgagtt cggcggggac gcgcaggcca cgatcgacgc | 660 |
| gatgatccaa acaccgtcg agcggatgta cgaggagacg gacgagaacc ggttcctcga | 720 |
| ggtcacctac gccaacggtg acaaggaggt cctgtacttc cgcgacttca actcgggcgc | 780 |

-continued

| | |
|---|---|
| gatgatccag aacatcgtgg accgggcgaa gaaggcggcg atcaagtcgg tgctggagac | 840 |
| caagcagccc ggtctgcggg tgcagcacct gctcgacgcg atcgtcgacg agttcgcgga | 900 |
| gaacgaggac ctgcccaaca ccaccaaccc ggacgactgg gcccggatct cgggcaagaa | 960 |
| gggcgagcgg atcgtctaca tccgcacgct ggtcaccggg aagaaccagg agtccggccg | 1020 |
| ggtcatcgac acggccacga acaccggcca gtacctgtaa ccgcaggtgg gccaggggag | 1080 |
| gccgccgatc cgtccgggtc ggcggcctcc gccgtgtcag gggcgcgccg cgcgccggcc | 1140 |
| cgcccagtag gcgagcagca ccccgccggc cacgaccagc atgcacccga tcatcagggg | 1200 |
| cacgttcggc ccggcgcagg acagcgagtc cggcgtgcag ctgcggaacg gcccgccctg | 1260 |
| cccgctggag tcgtaccgct ccgccgagaa caggaacacc agcaccgcca tgccgtgcac | 1320 |
| gggggcgagg aggaccgtca cggcgagcgc ggccgcgccg gcgcggagcc gtcggatgat | 1380 |
| cttgtcgggc acgtcgagaa gacgcttccc ggcggttccg gttgcccggc gtgtcgtccg | 1440 |
| ccggtggccg tataacgacc tatactgcgc gccatgaccg agcccgcggc cgagatccgc | 1500 |
| gccccgatca ccgaaaccga cgtcctggcc tggctcgagg agaccgcgca ggcggtccgc | 1560 |
| gcgcacgccg tcccgccgga ggagctgatc cggctgctgg gggagttgcg gcgcgcgtcg | 1620 |
| gcggcctgtg ccgacgcgtc ggactgggtg ctgctggcgg cgcgggagga gggggccagc | 1680 |
| ctgcgccaga tcgcgccggt cttcggcaag ggctacgtgc gggcgccggc ggcgcggctg | 1740 |
| gagaagctcc accggcaggc gctgaactcc gagcagtggc tggagatcct ccgtcaacga | 1800 |
| gcatcaggcg tataacgacc tatacgcggc ggctttcggc gaaaaaccac cggtggcccg | 1860 |
| ctccgcgggc gccccggaaa aacccgcacg gaaaggacag tcccctgcga atcggactcg | 1920 |
| gcctggcggc cctcgggcgg cccgcctata tcaacctcgg ccggagcagc gagctcccgg | 1980 |
| tccggcggga cgtgcggacg atgcgcgagg cgacgttcgc ggtgctcgac gcggcgtacg | 2040 |
| cggccggtgt gcgctggatc gacgtcgccc gctcctacgg ccgggccgag gagttcctgg | 2100 |
| ccgggtggct ggccgagcgc ggccacgcg acctcaccgt gtccagcaag tggggctaca | 2160 |
| cctacgtcgg cggctggcgc atggacgcca ccatgcacga ggtgaaggag cactcggcgg | 2220 |
| gcgtgttctc ccgccagtgg accgaaagcg gctcgctgct cggcaacgcc atcaacctct | 2280 |
| accaggtgca ctcgctcacc gtggacagcc cgttgttcac cgacgaggcg ctgcagcggg | 2340 |
| cgctggcggc gctcagcgac gacggcgtgc cgtcgggtt ctccacttcc gggccgaagc | 2400 |
| aggcggaggt gatccggcgg gcgttcgagc tggaagtggc cgggcggccg gtgttctcgg | 2460 |
| ccgtgcagtc gacctggaac ctgctcgaac cgtcggcagg cccggcgctc gcggaggcgc | 2520 |
| acgcggccgg gaacctggtg ctggtcaagg aaaccctcgc caacggcagg ctggtggtca | 2580 |
| acccgccgcc cgcgatcacc cgcctggcgc aacgctacgc agtcggcgcc gacgcggtgg | 2640 |
| cgatcgcggc ggtgctcgcc cagccgtggg cggacacggt cctcatcggc ccgtccagcc | 2700 |
| cgcagcagct ggccgccaac ctccgccgcg acggcgtcga cctgccacgg ggcgaactcg | 2760 |
| cggcgctgcg ggcgctggcc gagccgccgg aacggtactg ggatcggcga tcctcgctgc | 2820 |
| agtggcagtg aaggcttcga ctaatctcag cgcccacaac gcatactgaa gggaacgtca | 2880 |
| ccgtgcgtca tggagggatg gtggtcctgg ccgcggtcgt gctgaccggg ctcaccgggt | 2940 |
| gcgcggatcg cccgaacgac ctggagacct actacgacaa gccggcggac gcgacgacgc | 3000 |
| cggtgacggc gccgtcggtc tcgacgagcg tctcggtcgg ccaggcggcg gcgaacaccc | 3060 |
| cggtgaacca catcgccgag gacgtggcgg cggcggtgct caccaagagc gacctgtccg | 3120 |
| gcgagggcgt gcgggaggcg gcggcccgcg ccgccaacgg atcctgcttc gacgccgtgc | 3180 |

```
ccgccgggga cccgcgtggc tcgacctggc tctacaacag cggttcctcg ctgacgcagc    3240
aggtcaccgg ctacctcgac ccgcaccgcgg ccgaggtgct cgcgcaggtc gactgcgacg    3300
gcacggcgct gacggtcgcc cgcccggccg gcgcggaggc cgcgcgcgcc tggtgcgacg    3360
gcaccacctg cacgctgctg ctggccgcg ggcacgtgct gtccggcctg caggtcaccg    3420
cgagcacgca gaaccgggcc gcggaagcgg tgaagggcct ggcgtcgctg ccgccggga    3480 agctgccgcg gagctgaccg cccggacggg aaagcgctac ccgcggcgga accactcgtg    3540
gatcgcgtgc ctgccgtcgg gcacgaaagg gctttccggg tcctcgcga aggcccgcag    3600 ctcgtccagg ggcatccacc ggccggagac gatttcctcc ggctggtgga cgaccgggcc    3660
gtcccagcgc gcctcgtagg cgaagtagtg gcagcgcacc ggcggctgct cgaacgtgaa    3720
cgtgaacagg ggtcgcaggg gcacgccgcg cacgcccagt cctcggcca gctcccgttc    3780 cgcgccctcg gcgggtgctt cgcccgccgc gaccacgccg cccgcccagc agtcgtacag    3840
gccggggaag acgtccttgt ccggtgagcg ccggtgcacg tacacgcggg agccgtcccc    3900
ggagcgcacc agcaccagcg tcgcggcgtg ccagagcccc tgttcgcgca tgtcggcgcg    3960
gcgcacccgg ctcacgacca cgcccgcggc gtcgtagtgg gcgaccattt cctcagcact    4020
gctcaccatc ttgcgccagc atgacagatc cgggtgcttt acctggtcgc aaccggtggc    4080
ccactcaccg ttgccgcccg cgacccgtag gcttgggaca tgcggcggat catgggaacc    4140
gaagtcgagt acggcatcgc cgtgccgggc gacgcgacgg ccaacccggt actgacatcg    4200
acgcaggtcg tgctggccta cgcggcgcgc gcggacatcc cgcggggcgcg ccgcgcgcgg    4260 tgggactacg aggtggagtc gccgctgcgc gacgcccgtg gtttcgacct ggccggggccg    4320 ggcgggccgg ggcacgaccc ggacgtggag gacctcggcg cggccaacgt catcctgacc    4380
aacggcgccc ggctctacgt cgaccacgcg caccgggagt actcggcgcc cgaggtgacc    4440
aacccgcggg acggggtcat ctgggacaag gcgggcgagc gggtgatgga ggaggccgcg    4500
atgcgggcgg ccaccgtgcc cgggcagccg gtgctgcagc tgtacaagaa caacgtggac    4560
ggcaagggcg ccagctacgg cacccacgag aactacctga tggcccgttc gacgccgttc    4620
acctcggtga tcgccgggct gacgccgttc ttcgtgtccc ggcaggtggt gaccggttcc    4680
ggccgggtgg gtatcggccc gcagggtgag gaggccggct tccagctgtc gcagcgctcg    4740
gactacatcg aggtcgaggt cggcctggag acgacgctga gcggggggat catcaacacc    4800
cgcgacgagc cgcacgcgga c                                              4821
```

<210> SEQ ID NO 16
<211> LENGTH: 1048
<212> TYPE: DNA
<213> ORGANISM: Artificial Sequence
<220> FEATURE:
<223> OTHER INFORMATION: Synthetic Cloned vr1 in pSET152 vector

<400> SEQUENCE: 16

```
gagatctgtt gtgggctgga caatcgtgcc ggttggtagg atccagcggg taccaatacg     60
aaggaggcaa caagatgaga taccggcttt tcgggcgcac cggctgcgc gtggcggaga    120 tgttcctcgg ggcgatggcg ctgcaggaac cggacgaggc gcggcgggtg gtcaaggcct    180
acgccgacgc cggggggcaac gtgatcgaca cggcctcggc gtacgcggag agcgagaacg    240
tgctgggcga ggtgctgacc gaccgcgacc ggttcgtgct ggccaccaag tacacgctga    300
cgcgggatcc gcacgacccg aacgccgggg gcagccaccg caagaacctg gtcgcgtccc    360
```

| | |
|---|---|
| tggagcgcag cctgcggcgg ctgcgcaccg actacgtcga catcctgtgg gtgcacacgt | 420 |
| gggacccgca cacgccggtc gccgagacgc tgcgtgcgct ggacgacctg gtgcgggccg | 480 |
| ggaaggtcag gtacctcggg gtgtccgaca cgcccgcgtg ggtggtgagc cgggccgacg | 540 |
| tgctggcgga gtggcgcggg tggacgccgt tcgccggggt gcaggtgccc tacagcctgc | 600 |
| tgaaccgcga catcgagcgc gacgtgctgc cgatggccga gcagctgggg ctgaccgtcg | 660 |
| cggcgtgggg cgtcctggag cacgcgcgcg tgacccgggtc cagccgggtc ggttcgccgt | 720 |
| cgccggagca gcagcgggtg gcggcggcgg tgcgcgcggt ggcggacgag ctgggtgtca | 780 |
| cgccggcaca ggtggcgatc gcgtggcgc gggcgcggtc ggcggtcgtg cacccgctga | 840 |
| tcgggttccg gacggcggac cgggtcgcgg agagcgtcgc cgccctggac gtgacgctgc | 900 |
| ccccggaagc ggtggcgaag ctggaggcgg cggcgccgtt cgagccgggc ccgttcgccg | 960 |
| acttcgtgaa ccagtcggcg gccagcgccg gggtgttcgg ccacggcgag gtggtggcgc | 1020 |
| gtcagctgcg ggagtgatct agacctcc | 1048 |

<210> SEQ ID NO 17
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 17
ggatcccgcg cagctccggc gatcc                                          25

<210> SEQ ID NO 18
<211> LENGTH: 30
<212> TYPE: DNA
<213> ORGANISM: Artificial Sequence
<220> FEATURE:
<223> OTHER INFORMATION: Synthetic PCR_primer

<400> SEQUENCE: 18
gatatctgcg gtccactttg tcggaacgca                                     30

<210> SEQ ID NO 19
<211> LENGTH: 24
<212> TYPE: DNA
<213> ORGANISM: Artificial Sequence
<220> FEATURE:
<223> OTHER INFORMATION: Synthetic PCR_primer

<400> SEQUENCE: 19
gatatcggca gctcggcgac ggcg                                           24

<210> SEQ ID NO 20
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 20
aagcttgcgc caaggggcag ctgcg                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 21
ggatccgcgg cacacgcctc ggcgc                                    25

<210> SEQ ID NO 22
<211> LENGTH: 28
<212> TYPE: DNA
<213> ORGANISM: Artificial Sequence
<220> FEATURE:
<223> OTHER INFORMATION: Synthetic PCR_primer

<400> SEQUENCE: 22
gatatctgtc cggcagccta ccggaaat                                 28

<210> SEQ ID NO 23
<211> LENGTH: 27
<212> TYPE: DNA
<213> ORGANISM: Artificial Sequence
<220> FEATURE:
<223> OTHER INFORMATION: Synthetic PCR_primer

<400> SEQUENCE: 23
gatatccgat aggtttggcg ccgtgac                                  27

<210> SEQ ID NO 24
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 24
aagcttcgag cccggcgagg tgacg                                    25

<210> SEQ ID NO 25
<211> LENGTH: 27
<212> TYPE: DNA
<213> ORGANISM: Artificial Sequence
<220> FEATURE:
<223> OTHER INFORMATION: Synthetic PCR_primer

<400> SEQUENCE: 25
ggatccccga agtgctcgtc ggcgatc                                  27

<210> SEQ ID NO 26
<211> LENGTH: 27
<212> TYPE: DNA
<213> ORGANISM: Artificial Sequence
<220> FEATURE:
<223> OTHER INFORMATION: Synthetic PCR_primer

<400> SEQUENCE: 26
gatatctgca cagagagtag ctgcggc                                  27

<210> SEQ ID NO 27
<211> LENGTH: 26
<212> TYPE: DNA
<213> ORGANISM: Artificial Sequence
<220> FEATURE:
<223> OTHER INFORMATION: Synthetic PCR_primer

<400> SEQUENCE: 27
gatatcccgt ggggtggatg gcacgt                                   26

<210> SEQ ID NO 28

```
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 28
aagcttgcgg tggccgtgcc cgcga                                           25

<210> SEQ ID NO 29
<211> LENGTH: 27
<212> TYPE: DNA
<213> ORGANISM: Artificial Sequence
<220> FEATURE:
<223> OTHER INFORMATION: Synthetic PCR_primer

<400> SEQUENCE: 29
aagcttacgt caaccggaac gggttgc                                         27

<210> SEQ ID NO 30
<211> LENGTH: 29
<212> TYPE: DNA
<213> ORGANISM: Artificial Sequence
<220> FEATURE:
<223> OTHER INFORMATION: Synthetic PCR_primer

<400> SEQUENCE: 30
gatatctgga aatcccttct cggcttgtt                                       29

<210> SEQ ID NO 31
<211> LENGTH: 27
<212> TYPE: DNA
<213> ORGANISM: Artificial Sequence
<220> FEATURE:
<223> OTHER INFORMATION: Synthetic PCR_primer

<400> SEQUENCE: 31
aagcttcgca ccacgaggtg gagcccc                                         27

<210> SEQ ID NO 32
<211> LENGTH: 26
<212> TYPE: DNA
<213> ORGANISM: Artificial Sequence
<220> FEATURE:
<223> OTHER INFORMATION: Synthetic PCR_primer

<400> SEQUENCE: 32
ggatccggcc accgacagga ccgtca                                          26

<210> SEQ ID NO 33
<211> LENGTH: 27
<212> TYPE: DNA
<213> ORGANISM: Artificial Sequence
<220> FEATURE:
<223> OTHER INFORMATION: Synthetic PCR_primer

<400> SEQUENCE: 33
aagcttgcgg cagatcgagc agatccg                                         27

<210> SEQ ID NO 34
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 34
```

```
gatatctcgt ccgcacgtcc cgccg                                             25

<210> SEQ ID NO 35
<211> LENGTH: 28
<212> TYPE: DNA
<213> ORGANISM: Artificial Sequence
<220> FEATURE:
<223> OTHER INFORMATION: Synthetic PCR_primer

<400> SEQUENCE: 35
gatatcaggc ttcgactaat ctcagcgc                                          28

<210> SEQ ID NO 36
<211> LENGTH: 25
<212> TYPE: DNA
<213> ORGANISM: Artificial Sequence
<220> FEATURE:
<223> OTHER INFORMATION: Synthetic PCR_primer

<400> SEQUENCE: 36
agatctgtcc gcgtgcggct cgtcg                                             25
```